(12) United States Patent
Loring et al.

(10) Patent No.: US 11,723,676 B2
(45) Date of Patent: Aug. 15, 2023

(54) JOINT INSTRUMENTATION AND ASSOCIATED METHODS OF USE

(71) Applicant: Encore Medical, LP, Austin, TX (US)

(72) Inventors: Thomas Loring, Philadelphia, PA (US); Chulho Pak, Mahwah, NJ (US); Victor Chan, Landing, NJ (US); Ryan Sellman, Carlisle, PA (US)

(73) Assignee: ENCORE MEDICAL, L.P., Austin, TX (US)

( * ) Notice: Subject to any disclaimer, the term of this patent is extended or adjusted under 35 U.S.C. 154(b) by 295 days.

(21) Appl. No.: 17/230,158

(22) Filed: Apr. 14, 2021

(65) Prior Publication Data

US 2021/0290412 A1 Sep. 23, 2021

Related U.S. Application Data

(62) Division of application No. 16/223,864, filed on Dec. 18, 2018, now Pat. No. 11,000,296.
(Continued)

(51) Int. Cl.
*A61F 2/46* (2006.01)
*A61F 2/42* (2006.01)
(Continued)

(52) U.S. Cl.
CPC .......... *A61B 17/17* (2013.01); *A61B 17/1775* (2016.11); *A61F 2/4606* (2013.01);
(Continued)

(58) Field of Classification Search
CPC ............................ A61B 17/17; A61B 17/1775
See application file for complete search history.

(56) References Cited

U.S. PATENT DOCUMENTS 1,505,106 A 8/1924 Schroder
3,839,742 A 10/1974 Link
(Continued)

FOREIGN PATENT DOCUMENTS

EP 0554959 A1 8/1993
EP 1468652 A1 10/2004
(Continued)

OTHER PUBLICATIONS

Extended European Search Report for Application No. EP 18213765.3 dated May 24, 2019, pp. 1-6.
(Continued)

*Primary Examiner* — Christian A Sevilla
(74) *Attorney, Agent, or Firm* — Veros Legal Solutions, LLP

(57) ABSTRACT

A trial implant is provided. The implant includes a central portion. The central portion includes a top articulating surface extending between a first end and a second end and having a convex shape, a bottom surface configured to at least partially contact a first resected surface of a bone, and a first side surface extending between the top articulating surface and the bottom surface. The first side surface is sloped such that a width of the top articulating surface is greater than a width of the bottom surface. The implant further includes a first outer portion extending laterally from the central portion. The first side surface and the first outer portion are separated by a first opening shaped such that up to four resected surfaces of the bone are visible when the trial implant is seated on the bone.

20 Claims, 20 Drawing Sheets

Related U.S. Application Data

(60) Provisional application No. 62/673,285, filed on May 18, 2018, provisional application No. 62/608,252, filed on Dec. 20, 2017.

(51) Int. Cl.
  *A61B 17/17* (2006.01)
  *A61F 2/30* (2006.01)
  *A61B 17/15* (2006.01)

(52) U.S. Cl.
  CPC .......... *A61F 2/4657* (2013.01); *A61F 2/4684* (2013.01); *A61B 17/15* (2013.01); *A61F 2/4202* (2013.01); *A61F 2002/30878* (2013.01); *A61F 2002/4205* (2013.01); *A61F 2002/4207* (2013.01); *A61F 2002/4668* (2013.01)

(56) References Cited

U.S. PATENT DOCUMENTS

| | | |
|---|---|---|
| 3,975,778 A | 8/1976 | Newton, III |
| 3,987,500 A | 10/1976 | Schlein |
| 4,021,864 A | 5/1977 | Waugh |
| 4,069,518 A | 1/1978 | Groth, Jr. et al. |
| 4,156,944 A | 6/1979 | Dexel et al. |
| 4,166,292 A | 9/1979 | Bokros |
| 4,229,839 A | 10/1980 | Schwemmer |
| 4,232,404 A | 11/1980 | Samuelson et al. |
| 4,289,123 A | 9/1981 | Dunn |
| 4,301,552 A | 11/1981 | London |
| 4,499,900 A | 2/1985 | Petrofsky et al. |
| 4,501,269 A | 2/1985 | Bagby |
| 4,524,766 A | 6/1985 | Petersen |
| 4,569,352 A | 2/1986 | Petrofsky et al. |
| 4,570,927 A | 2/1986 | Petrofsky et al. |
| 4,586,495 A | 5/1986 | Petrofsky |
| 4,655,778 A | 4/1987 | Koeneman |
| 4,697,808 A | 10/1987 | Larson et al. |
| 4,711,242 A | 12/1987 | Petrofsky |
| 4,990,161 A | 2/1991 | Kampner |
| 5,020,519 A | 6/1991 | Kyle et al. |
| 5,041,139 A | 8/1991 | Braanemark |
| 5,063,937 A | 11/1991 | Ezenwa et al. |
| 5,074,285 A | 12/1991 | Wright |
| 5,122,144 A | 6/1992 | Bert et al. |
| 5,219,364 A | 6/1993 | Lloyd |
| 5,326,365 A | 7/1994 | Alvine |
| 5,336,270 A | 8/1994 | Lloyd |
| 5,344,423 A | 9/1994 | Dietz et al. |
| 5,431,653 A | 7/1995 | Callaway |
| 5,474,559 A | 12/1995 | Bertin et al. |
| 5,486,180 A | 1/1996 | Dietz et al. |
| 5,514,139 A | 5/1996 | Goldstein et al. |
| 5,571,109 A | 11/1996 | Bertagnoli |
| 5,571,184 A | 11/1996 | Desatnick |
| 5,630,820 A | 5/1997 | Todd |
| 5,649,929 A | 7/1997 | Callaway |
| 5,662,656 A | 9/1997 | White |
| 5,766,259 A | 6/1998 | Sammarco |
| 5,810,827 A | 9/1998 | Haines et al. |
| 5,824,106 A | 10/1998 | Fournol |
| 5,885,299 A | 3/1999 | Winslow et al. |
| 5,916,216 A | 6/1999 | Desatnick et al. |
| 5,993,487 A | 11/1999 | Skardoutos et al. |
| 6,053,945 A | 4/2000 | O'neil et al. |
| 6,090,114 A | 7/2000 | Matsuno et al. |
| 6,099,571 A | 8/2000 | Knapp |
| 6,113,639 A | 9/2000 | Ray et al. |
| 6,174,314 B1 | 1/2001 | Waddell |
| 6,183,519 B1 | 2/2001 | Bonnin et al. |
| 6,245,109 B1 | 6/2001 | Mendes et al. |
| 6,284,001 B1 | 9/2001 | Knapp |
| 6,409,767 B1 | 6/2002 | Pericé et al. |
| 6,482,236 B2 | 11/2002 | Habecker |
| 6,520,967 B1 | 2/2003 | Cauthen |
| 6,551,316 B1 | 4/2003 | Rinner et al. |
| 6,554,837 B1 | 4/2003 | Hauri et al. |
| 6,610,095 B1 | 8/2003 | Pope et al. |
| 6,663,669 B1 | 12/2003 | Reiley |
| 6,673,116 B2 | 1/2004 | Reiley |
| 6,686,437 B2 | 2/2004 | Buchman et al. |
| 6,699,289 B2 | 3/2004 | Iannotti et al. |
| 6,755,841 B2 | 6/2004 | Fraser et al. |
| 6,852,130 B2 | 2/2005 | Keller et al. |
| 6,860,902 B2 | 3/2005 | Reiley |
| 6,863,691 B2 | 3/2005 | Short et al. |
| 6,866,683 B2 | 3/2005 | Gerbec et al. |
| 6,875,236 B2 | 4/2005 | Reiley |
| 6,887,276 B2 | 5/2005 | Gerbec et al. |
| 6,911,047 B2 | 6/2005 | Rockwood et al. |
| 6,926,739 B1 | 8/2005 | O'connor et al. |
| 6,939,380 B2 | 9/2005 | Guzman |
| 7,011,687 B2 | 3/2006 | Deffenbaugh et al. |
| 7,025,790 B2 | 4/2006 | Parks et al. |
| 7,060,074 B2 | 6/2006 | Rosa et al. |
| 7,118,580 B1 | 10/2006 | Beyersdorff et al. |
| 7,141,053 B2 | 11/2006 | Rosa et al. |
| 7,160,328 B2 | 1/2007 | Rockwood, Jr. et al. |
| 7,204,851 B2 | 4/2007 | Trieu et al. |
| 7,297,165 B1 | 11/2007 | Kriek |
| 7,314,488 B2 | 1/2008 | Reiley |
| 7,323,012 B1 | 1/2008 | Stone et al. |
| 7,361,194 B2 | 4/2008 | Carroll |
| 7,419,491 B2 | 9/2008 | Masini |
| 7,465,303 B2 | 12/2008 | Riccione et al. |
| 7,468,075 B2 | 12/2008 | Lang et al. |
| 7,470,273 B2 | 12/2008 | Dougherty-Shah |
| 7,485,147 B2 | 2/2009 | Pappas et al. |
| 7,491,205 B1 | 2/2009 | Michelson |
| 7,510,557 B1 | 3/2009 | Bonutti |
| 7,534,246 B2 | 5/2009 | Railey et al. |
| 7,534,270 B2 | 5/2009 | Ball |
| 7,537,664 B2 | 5/2009 | O'neill et al. |
| 7,618,451 B2 | 11/2009 | Berez et al. |
| 7,625,409 B2 | 12/2009 | Saltzman et al. |
| 7,628,818 B2 | 12/2009 | Hazebrouck et al. |
| 7,632,279 B2 | 12/2009 | Bastian |
| 7,641,697 B2 | 1/2010 | Reiley |
| 7,717,920 B2 | 5/2010 | Reiley |
| 7,744,601 B2 | 6/2010 | Rosa et al. |
| 7,842,092 B2 | 11/2010 | Otto et al. |
| 7,867,281 B2 | 1/2011 | Carroll |
| 7,914,583 B2 | 3/2011 | Wolfe et al. |
| 7,918,894 B2 | 4/2011 | Wolfe et al. |
| 7,963,996 B2 | 6/2011 | Saltzman et al. |
| 8,002,841 B2 | 8/2011 | Hasselman |
| 8,034,114 B2 | 10/2011 | Reiley |
| 8,048,164 B2 | 11/2011 | Reiley |
| 8,114,091 B2 | 2/2012 | Ratron et al. |
| 8,128,703 B2 | 3/2012 | Hazebrouck et al. |
| 8,241,360 B2 | 8/2012 | Bao et al. |
| 8,267,975 B2 | 9/2012 | Mccombs et al. |
| 8,268,007 B2 | 9/2012 | Barsoum et al. |
| 8,277,448 B2 | 10/2012 | Daluiski et al. |
| 8,282,590 B2 | 10/2012 | Goswami et al. |
| 8,313,492 B2 | 11/2012 | Wong et al. |
| 8,388,684 B2 | 3/2013 | Bao et al. |
| 8,403,935 B2 | 3/2013 | Gross |
| 8,430,930 B2 | 4/2013 | Hunt |
| 8,460,304 B2 | 6/2013 | Fitz et al. |
| 8,470,047 B2 | 6/2013 | Hazebrouck et al. |
| 8,480,755 B2 | 7/2013 | Reiley |
| 8,496,712 B2 | 7/2013 | Reiley |
| 8,496,713 B2 | 7/2013 | Bennett et al. |
| 8,545,501 B2 | 10/2013 | Wong |
| 8,556,983 B2 | 10/2013 | Bojarski et al. |
| 8,585,744 B2 | 11/2013 | Duggal et al. |
| 8,597,361 B2 | 12/2013 | Sidebotham et al. |
| 8,617,172 B2 | 12/2013 | Fitz et al. |
| 8,632,600 B2 | 1/2014 | Zannis et al. |
| 8,668,743 B2 | 3/2014 | Perler |
| 8,715,359 B2 | 5/2014 | Deffenbaugh et al. |
| 8,728,387 B2 | 5/2014 | Jones et al. |

(56) References Cited

U.S. PATENT DOCUMENTS

| | | |
|---|---|---|
| 8,871,142 B2 | 10/2014 | Smith et al. |
| 8,998,991 B2 | 4/2015 | Bennett et al. |
| 9,011,503 B2 | 4/2015 | Duggal et al. |
| 9,101,476 B2 | 8/2015 | Deruntz et al. |
| 9,119,734 B2 | 9/2015 | Dees |
| 9,125,672 B2 | 9/2015 | Fitz et al. |
| 9,144,500 B2 | 9/2015 | Harding, Jr. |
| 9,180,010 B2 | 11/2015 | Dong et al. |
| 9,180,012 B2 | 11/2015 | Jordan et al. |
| 9,186,154 B2 | 11/2015 | Li |
| 9,204,967 B2 | 12/2015 | Wyss et al. |
| 9,216,085 B2 | 12/2015 | Schwartz et al. |
| 9,237,953 B2 | 1/2016 | Rybolt et al. |
| 9,265,611 B2 | 2/2016 | Schwartz et al. |
| 9,393,028 B2 | 7/2016 | Schuster |
| 9,421,108 B2 | 8/2016 | Hunt et al. |
| 9,456,901 B2 | 10/2016 | Jones et al. |
| 9,526,619 B2 | 12/2016 | Schwartz et al. |
| 9,539,115 B2 | 1/2017 | Coulange et al. |
| 9,668,746 B2 | 6/2017 | Lee et al. |
| 9,681,955 B2 | 6/2017 | Jordan et al. |
| 9,907,561 B2 | 3/2018 | Luna et al. |
| 9,968,376 B2 | 5/2018 | Metzger et al. |
| 9,974,588 B2 | 5/2018 | Stemniski et al. |
| 9,993,255 B2 | 6/2018 | Mcginley et al. |
| 9,999,516 B2 | 6/2018 | Hunt et al. |
| 10,080,573 B2 | 9/2018 | McGinley et al. |
| 10,106,724 B2 | 10/2018 | Dams et al. |
| 10,772,730 B2 | 9/2020 | Mccleary et al. |
| 2001/0029377 A1 * | 10/2001 | Aebi ............... A61B 17/025 606/105 |
| 2001/0031969 A1 | 10/2001 | Aebi et al. |
| 2002/0116009 A1 | 8/2002 | Fraser et al. |
| 2002/0143343 A1 | 10/2002 | Castro |
| 2003/0212403 A1 | 11/2003 | Swanson |
| 2004/0030399 A1 | 2/2004 | Asencio |
| 2004/0102785 A1 | 5/2004 | Hodorek et al. |
| 2004/0117019 A1 | 6/2004 | Trieu et al. |
| 2004/0122519 A1 | 6/2004 | Wiley et al. |
| 2004/0167631 A1 | 8/2004 | Luchesi et al. |
| 2004/0186585 A1 | 9/2004 | Feiwell |
| 2004/0220582 A1 | 11/2004 | Keller |
| 2004/0249388 A1 | 12/2004 | Michelson |
| 2005/0004676 A1 | 1/2005 | Schon et al. |
| 2005/0027360 A1 | 2/2005 | Webb et al. |
| 2005/0033442 A1 | 2/2005 | Fisher et al. |
| 2005/0049710 A1 | 3/2005 | O'driscoll et al. |
| 2005/0055028 A1 | 3/2005 | Haines et al. |
| 2005/0113842 A1 | 5/2005 | Bertagnoli et al. |
| 2005/0119665 A1 | 6/2005 | Keller |
| 2005/0165408 A1 | 7/2005 | Puno et al. |
| 2005/0245928 A1 | 11/2005 | Colleran et al. |
| 2005/0288792 A1 * | 12/2005 | Landes ............ A61B 17/1682 623/21.18 |
| 2006/0004362 A1 | 1/2006 | Patterson et al. |
| 2006/0004377 A1 | 1/2006 | Keller |
| 2006/0020345 A1 | 1/2006 | O'connor et al. |
| 2006/0041311 A1 | 2/2006 | Mcleer |
| 2006/0100634 A1 | 5/2006 | Ferguson |
| 2006/0136058 A1 | 6/2006 | Pietrzak |
| 2006/0142870 A1 | 6/2006 | Robinson et al. |
| 2006/0149278 A1 | 7/2006 | Abdou |
| 2006/0195116 A1 | 8/2006 | Fox |
| 2006/0235421 A1 | 10/2006 | Rosa et al. |
| 2006/0241634 A1 | 10/2006 | Tuttle et al. |
| 2006/0247788 A1 | 11/2006 | Ross |
| 2007/0038303 A1 | 2/2007 | Myerson et al. |
| 2007/0088442 A1 | 4/2007 | Cima et al. |
| 2007/0123879 A1 | 5/2007 | Songer et al. |
| 2007/0123901 A1 | 5/2007 | Foley et al. |
| 2007/0135924 A1 | 6/2007 | Verhoogen |
| 2007/0173944 A1 | 7/2007 | Keller et al. |
| 2007/0191857 A1 | 8/2007 | Allard et al. |
| 2007/0198025 A1 | 8/2007 | Trieu et al. |
| 2007/0233140 A1 | 10/2007 | Metzger et al. |
| 2008/0015603 A1 | 1/2008 | Collazo |
| 2008/0097617 A1 | 4/2008 | Fellinger et al. |
| 2008/0109081 A1 | 5/2008 | Bao et al. |
| 2008/0167655 A1 | 7/2008 | Wang et al. |
| 2008/0177272 A1 | 7/2008 | Zucherman et al. |
| 2008/0177275 A1 | 7/2008 | Wing et al. |
| 2008/0200988 A1 | 8/2008 | Carroll |
| 2008/0215156 A1 | 9/2008 | Duggal et al. |
| 2008/0269756 A1 | 10/2008 | Tomko et al. |
| 2008/0275452 A1 | 11/2008 | Lang et al. |
| 2008/0306605 A1 | 12/2008 | Hasselman |
| 2008/0312745 A1 | 12/2008 | Keller et al. |
| 2009/0018665 A1 | 1/2009 | Clifford et al. |
| 2009/0030422 A1 | 1/2009 | Parsons et al. |
| 2009/0048603 A1 | 2/2009 | Hoag et al. |
| 2009/0054992 A1 | 2/2009 | Landes et al. |
| 2009/0082875 A1 * | 3/2009 | Long ............... A61F 2/4202 623/21.18 |
| 2009/0132047 A1 | 5/2009 | Mansmann et al. |
| 2009/0138021 A1 | 5/2009 | Colquhoun et al. |
| 2009/0182433 A1 | 7/2009 | Reiley et al. |
| 2009/0198341 A1 | 8/2009 | Choi et al. |
| 2009/0234362 A1 | 9/2009 | Blain et al. |
| 2009/0270869 A1 | 10/2009 | Colquhoun et al. |
| 2009/0275951 A1 | 11/2009 | Arcenio et al. |
| 2009/0276052 A1 | 11/2009 | Regala et al. |
| 2009/0306671 A1 | 12/2009 | Mccormack et al. |
| 2009/0306675 A1 | 12/2009 | Wong et al. |
| 2009/0306781 A1 | 12/2009 | Kyomoto et al. |
| 2010/0023066 A1 | 1/2010 | Long et al. |
| 2010/0057216 A1 | 3/2010 | Gannoe et al. |
| 2010/0069910 A1 | 3/2010 | Hasselman |
| 2010/0100097 A1 | 4/2010 | Wong |
| 2010/0100134 A1 | 4/2010 | Mocanu |
| 2010/0130983 A1 | 5/2010 | Thornhill et al. |
| 2010/0191244 A1 | 7/2010 | White et al. |
| 2010/0198355 A1 | 8/2010 | Kofoed et al. |
| 2010/0204799 A1 | 8/2010 | Keller et al. |
| 2010/0212138 A1 | 8/2010 | Carroll et al. |
| 2010/0217338 A1 | 8/2010 | Carroll et al. |
| 2010/0318088 A1 | 12/2010 | Warne et al. |
| 2011/0009964 A1 | 1/2011 | Schwartz et al. |
| 2011/0035019 A1 | 2/2011 | Goswami et al. |
| 2011/0112542 A1 | 5/2011 | Gross |
| 2011/0118792 A1 | 5/2011 | Orsak et al. |
| 2011/0125275 A1 | 5/2011 | Lipman et al. |
| 2011/0172780 A1 | 7/2011 | Scheland |
| 2011/0218542 A1 * | 9/2011 | Lian ............... A61B 17/1775 606/88 |
| 2011/0295380 A1 | 12/2011 | Long |
| 2011/0313469 A1 | 12/2011 | Mccombs et al. |
| 2011/0313532 A1 | 12/2011 | Hunt |
| 2011/0320005 A1 * | 12/2011 | Rydell ............. A61B 17/562 623/21.18 |
| 2012/0010718 A1 | 1/2012 | Still |
| 2012/0109326 A1 | 5/2012 | Peder |
| 2012/0130376 A1 | 5/2012 | Loring et al. |
| 2012/0130434 A1 | 5/2012 | Stemniski et al. |
| 2012/0191210 A1 | 7/2012 | Ratron et al. |
| 2012/0221008 A1 | 8/2012 | Carroll et al. |
| 2012/0245701 A1 | 9/2012 | Zak et al. |
| 2012/0271314 A1 | 10/2012 | Stemniski et al. |
| 2012/0271430 A1 | 10/2012 | Arnett et al. |
| 2013/0030529 A1 | 1/2013 | Hunt |
| 2013/0041473 A1 | 2/2013 | Rouyer et al. |
| 2013/0090739 A1 | 4/2013 | Linares et al. |
| 2013/0103037 A1 | 4/2013 | Wong et al. |
| 2013/0116692 A1 | 5/2013 | Daluiski et al. |
| 2013/0116797 A1 | 5/2013 | Coulange et al. |
| 2013/0123935 A1 | 5/2013 | Hunt et al. |
| 2013/0158672 A1 | 6/2013 | Hunt |
| 2013/0184830 A1 | 7/2013 | Hazebrouck et al. |
| 2013/0197517 A1 | 8/2013 | Gross |
| 2013/0218275 A1 | 8/2013 | Caballes |
| 2013/0325009 A1 | 12/2013 | Duggal et al. |
| 2014/0107794 A1 | 4/2014 | Deffenbaugh et al. |
| 2014/0128985 A1 | 5/2014 | Sanders et al. |
| 2014/0188236 A1 | 7/2014 | Mcginley et al. |
| 2014/0207244 A1 | 7/2014 | Sanders et al. |

(56) References Cited

U.S. PATENT DOCUMENTS

| | | |
|---|---|---|
| 2014/0336658 A1 | 11/2014 | Luna et al. |
| 2014/0350688 A1 | 11/2014 | Michel et al. |
| 2015/0045902 A1 | 2/2015 | Perler et al. |
| 2015/0157339 A1 | 6/2015 | Mcginley et al. |
| 2015/0157463 A1 | 6/2015 | Stad et al. |
| 2015/0157467 A1 | 6/2015 | Mcginley et al. |
| 2015/0173912 A1 | 6/2015 | Bennett et al. |
| 2015/0282946 A1 | 10/2015 | Hunt |
| 2015/0313715 A1 | 11/2015 | Wainscott et al. |
| 2015/0320567 A1 | 11/2015 | Terrill et al. |
| 2016/0135957 A1 | 5/2016 | Schwartz et al. |
| 2017/0000503 A1 | 1/2017 | Keefer et al. |
| 2017/0095341 A1* | 4/2017 | Smith ............... A61F 2/4684 |
| 2017/0156875 A9 | 6/2017 | Reiley et al. |
| 2017/0325826 A1* | 11/2017 | Bake ............... A61B 17/1775 |
| 2020/0129213 A1 | 4/2020 | Singh et al. |

FOREIGN PATENT DOCUMENTS

| | | |
|---|---|---|
| EP | 2777627 A1 | 9/2014 |
| FR | 2770393 A1 | 5/1999 |
| WO | 9723172 A2 | 7/1997 |
| WO | 9965403 A1 | 12/1999 |
| WO | 2006052571 A2 | 5/2006 |
| WO | 2007092728 A1 | 8/2007 |
| WO | 2008076559 A1 | 6/2008 |
| WO | 2008078082 A2 | 7/2008 |
| WO | 2008157415 A1 | 12/2008 |
| WO | 2009015009 A1 | 1/2009 |
| WO | 2009158522 A1 | 12/2009 |

OTHER PUBLICATIONS

Extended European Search Report for Application No. EP09771054 dated Feb. 11, 2015.

International Search Report and Written Opinion dated Oct. 20, 2009 for PCT/US2009/048669.

International Search Report dated Oct. 20, 2000 for PCT/US2009/048699.

Link S.T.A.R. Scandinavian Total Ankle Replacement Brochure; Waldemar Link GmbH & Co.; Hamburg, Germany;1990.

Link S.T.A.R. Scandinavian Total Ankle Replacement Brochure; Waldemar Link GmbH & Co.; Hamburg, Germany;1993.

Small Bones Innovations, Inc., Star™ Surgical Technique, 2009-2013.

StarTM Total Ankle Replacement, Operative Technique, May 2017 Stryker, pp. 1-32.

* cited by examiner

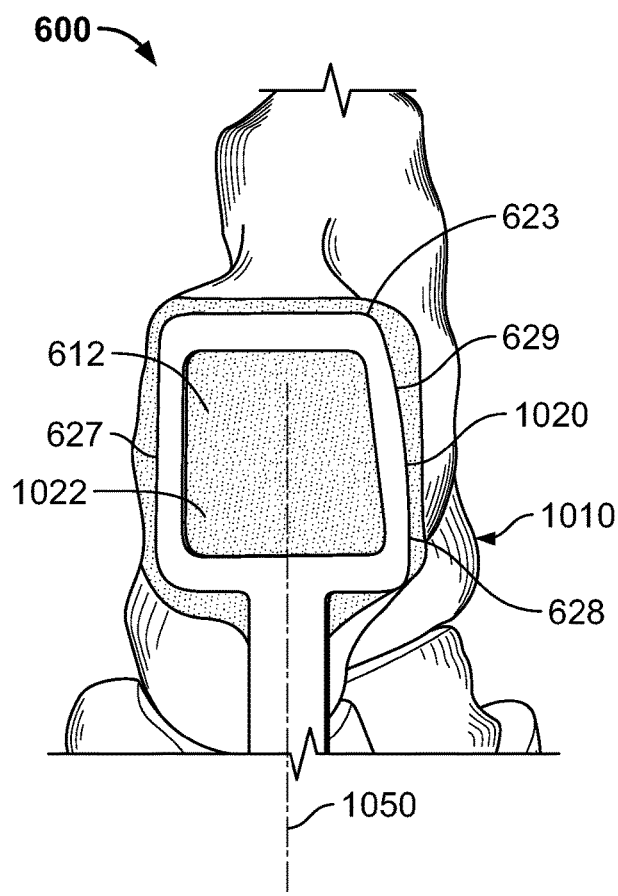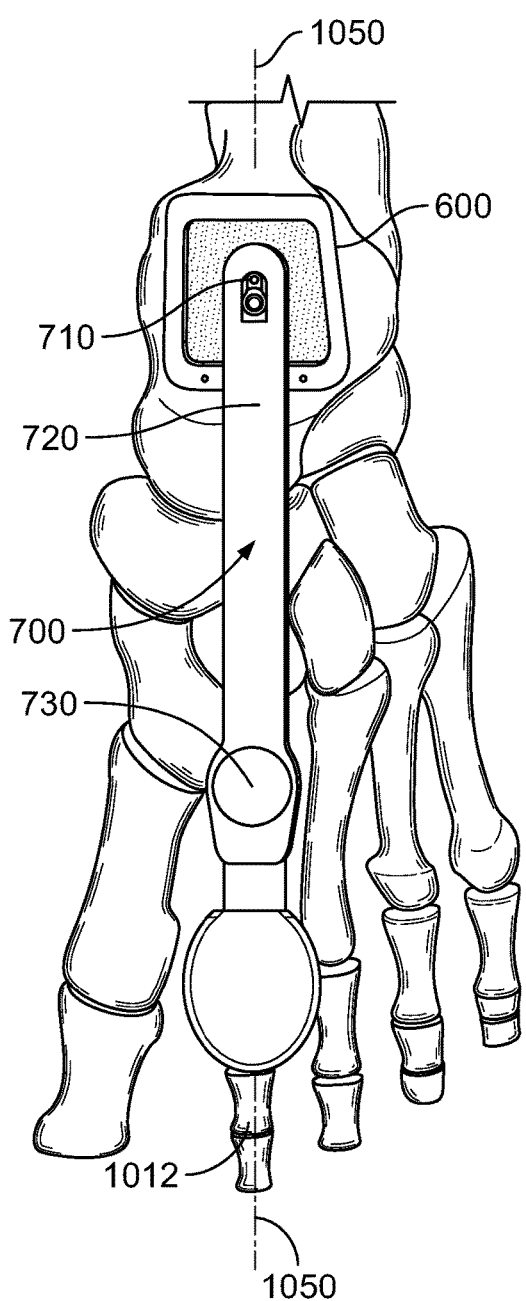
FIG. 31
FIG. 32

JOINT INSTRUMENTATION AND ASSOCIATED METHODS OF USE

CROSS-REFERENCE TO RELATED APPLICATIONS

This application is a divisional of, and claims the benefit of the filing date of U.S. patent application Ser. No. 16/223,864, filed Dec. 18, 2018 and entitled "Joint Instrumentation and Associated Methods of Use," which claims the benefit of the filing date of U.S. Provisional Patent Application No. 62/673,285, filed on May 18, 2018 and entitled "Joint Space Evaluator and Bone Resection Template" and U.S. Provisional Patent Application No. 62/608,252, filed on Dec. 20, 2017 and entitled "Joint Instrumentation and Associated Methods of Use," the disclosures of all of which are hereby incorporated by reference herein in their entirety.

BACKGROUND OF THE INVENTION

The present disclosure relates to trial implants, implants, tools, instruments and other devices used in joint replacement surgery along with associated methods of use.

A variety of devices and techniques for their use are known for repairing or replacing joints, such as the ankle joint. Repair or replacement of the ankle joint requires that the talar bone be prepared for placement of a talar implant. Typically, such a process involves resection of the talus to create one or more planar surfaces so that an implant may be secured thereon. Although devices and techniques are available to prepare a resected talar surface for mounting of instruments to perform the various resections around the talus, one of the more difficult aspects of the technique is properly aligning the talus relative to the tibia and properly setting a reference location, such as a datum, for the placement of resection instrumentation to perform accurate cuts of the talus.

In particular, existing techniques for verifying soft tissue balancing on the medial and lateral sides of an ankle are often cumbersome, such as the performance of a range of motion test using a trial implant. The range of motion test is often time consuming and requires an initial placement of a trial before it can be performed. Additionally, when using a template with a full body structure at its insertion end to determine an implant size after an initial talar resection, the template typically must be removed prior to identifying a centerline of the resected surface for placement of resection instrumentation and for drilling of holes for a datum. Moreover, such a template often provides no visibility within its outer perimeter at its insertion end.

Additionally, although devices and techniques are available to secure a talar implant in place on a resected surface of the talus, it is often difficult to achieve accurate placement of the implant. With existing approaches, use of the resected surfaces of the talus to verify the seating of the talar implant is not possible or has limited application, at best. Moreover, existing approaches are limited in their capacity to evaluate an expected range of motion of the ankle, or the accuracy of the formed resected surfaces, with the new implant prior to final placement of the implant. Moreover, because many existing talar implants do not include spikes, little consideration has been given to the formation of holes in the talus for the securement of an implant.

Thus, a need exists for improved devices and related surgical techniques for joint replacement, particularly improvements to implant placement, performance and overall simplification in the performance of joint surgery.

BRIEF SUMMARY OF THE INVENTION

In one embodiment, the present disclosure relates to a trial implant having a plurality of windows. When the trial implant is secured on a resected talus, one or more resected surfaces are visible through each window. Thus, windows expose top, medial, lateral, anterior and/or posterior facing resected surfaces of the talus. The trial implant includes an articulating upper, or top, surface that corresponds to a surface of a permanent implant. In another embodiment, methods employing the trial implant allow for more accurate positioning of the implant, ensuring it will seat correctly. Additionally, with the trial implant in place, a range of motion of the ankle may be evaluated prior to placement of the permanent implant.

In another embodiment, the present disclosure relates to a trial implant that includes a central portion and an outer portion. The central portion includes a top surface extending between a first end and a second end. The top surface has a convex shape, a bottom surface configured to at least partially contact a first resected surface of a bone, and a side surface extending between the top surface and the bottom surface. The outer portion extends laterally from the central portion. The side surface and the outer portion are separated by an opening. The top surface is an articulating surface. The side surface is sloped such that a width of the top surface is greater than a width of the bottom surface. The opening is shaped so that up to four resected surfaces are visible when the trial implant is seated on a bone having a plurality of resected surfaces.

In some arrangements, the trial implant may include a second opening. The second opening may be smaller than the first opening. In some arrangements, the trial implant may include a second opening located in between the central portion and the outer portion. The first opening may be positioned relative to the second opening so that a second resected surface of the bone is visible through the first opening and a third resected surface of the bone is visible through the second opening when the trial implant is positioned on the bone. The first opening may be sized and shaped so that the first resected surface, the second resected surface, a fourth resected surface and a fifth resected surface are visible through the first opening when the trial implant is positioned on the bone. In some arrangements, the outer portion extends laterally from the central portion such that the outer portion is entirely on one side of a plane defining an outer surface of the side surface. In some arrangements, the outer portion forms a perimeter around the central portion. In some arrangements, the trial implant is monolithic. In still further examples, the outer portion includes a top surface and a bottom surface which face in the same direction as the top surface and bottom surface of the central portion, respectively. Each of the top surfaces and bottom surfaces of both the central portion and outer portion may have a width that is larger than a height of the side surface of the central portion or a side surface of the outer portion, respectively.

In some arrangements, the trial implant may include a second outer portion that extends laterally from the central portion such that the central portion separates the second outer portion from the outer portion. In these arrangements, the second opening separates the central portion from the second outer portion. In some examples, the trial implant may also include a third opening located through the central portion. The third opening may have a long dimension transverse to a long dimension of the second opening. In other examples, the outer portion may have a first shape and the second outer portion may have a second shape, the first shape different than the second shape. In further arrangements, the outer portion may extend laterally from the central portion such that the outer portion is entirely on one side of a plane through the side surface.

In another embodiment, the present disclosure relates to a surgical guide structure. The surgical guide structure includes a plurality of windows sized and positioned so that one or more resected surfaces of a talus are visible when the surgical guide structure is secured thereon. At least two resected surfaces are visible from each of two windows, where a medial and top resected surface are visible through one window and a lateral and top resected surface are visible through the other window. The surgical guide structure also includes a plurality of apertures, where there are at least two types of apertures among the plurality. At least one aperture is defined by a varying angle perimeter wall so that part of the wall is sloped at an acute angle relative to an upper surface of the surgical guide structure whereas another part of the wall is perpendicular to the upper surface of the surgical guide structure. In another embodiment, a method of using the surgical guide structure involves alignment and securement of the surgical guide structure onto a resected talar bone and drilling of holes through one or more of the apertures. The windows of the structure may be used to align and otherwise position the surgical guide structure on the bone to improve the accuracy of the drill locations. Where there is inadequate room at the surgical site to drill perpendicular to the top surface of the talus near its posterior end, holes into the bone may be drilled at an acute angle to reduce the invasiveness of the procedure.

In one embodiment, the present disclosure relates to a surgical guide structure that includes a body with a first and second aperture and a first and second opening. The first aperture is through the body and is sized for placement of a drill bit therethrough. The second aperture is through the body at an angle relative to a top surface of the body. The second aperture is parallel to the first aperture and is symmetrical to the first aperture about a central axis through the body. The first opening is sized and positioned so that when the surgical guide structure is positioned on a first resected surface of a bone, the first resected surface and a second resected surface of the bone are visible through the first opening. The second opening is positioned opposite the first opening so that a third resected surface of the bone is visible through the second opening. In this arrangement, the first opening extends partially in between the first aperture and the second aperture.

Turning to the details of the body, the body includes a main body and an outer portion arranged such that the first opening defines a space therebetween. The first opening extends along a portion of an edge of the main body and along a portion of an edge of the outer portion. At least part of the edge of the main body and at least part of the edge of the outer portion contact first and second resected surfaces, respectively, when the surgical guide structure is positioned on the first resected surface. The first opening includes a perimeter defined by the portion of the edge of the main body and the portion of the edge of the outer portion includes a length with at least one linear portion and at least one curved portion.

In one embodiment, the present disclosure relates to a surgical guide structure that includes a body, at least one aperture through the body and an opening. The at least one aperture is sized for placement of a drill bit therethrough. The opening is sized and positioned so that when the surgical guide structure is positioned on a first resected surface of a bone, the first resected surface and a second resected surface of the bone are visible through the opening.

In some arrangements, the aperture through the body of the surgical guide structure may be transverse relative to a top surface of the body. In other examples, the surgical guide structure may also include a second aperture that is transverse to the first aperture. In other examples, the second aperture may be orthogonal to the top surface of the body. In still further arrangements, the surgical guide structure may include a second opening positioned opposite the first opening so that a third resected surface of the bone is visible through the second opening. In other examples, the surgical guide structure may include a second aperture through the body of the surgical guide structure at an angle relative to a top surface of the body and parallel to the first aperture. The second aperture may be symmetrical to the first aperture about a central axis through the body.

In some arrangements, the body of the surgical guide structure may also include a main body and an outer portion arranged such that the opening defines a space therebetween. In some examples, the opening may extend along a portion of an edge of the main body and along a portion of an edge of the outer portion. In still further examples, at least part of the edge of the main body and at least part of the edge of the outer portion contact first and second resected surfaces, respectively, when the surgical guide structure is positioned on the first resected surface. In other examples, the opening may extend partially in between the first aperture and a second aperture. In other examples, the first aperture may be transverse to the second aperture.

In some arrangements, the opening of the surgical guide structure may include a perimeter defined by an edge that includes a length with at least one linear portion and at least one curved portion. In some examples, the edge may include a first location on its length that is at a first distance from a bottom surface of the guide configured to contact bone and a second location on its length that is at a second distance from the bottom surface of the guide.

In one embodiment, the present disclosure relates to a surgical guide structure that includes a body, a first aperture and a second aperture. The body is configured for placement on a prepared bone surface so that at least part of a bottom surface of the body corresponds to the prepared bone surface when the body is positioned on the bone surface. The first aperture is located through the body and is sized for the placement of a drill bit therethrough. The second aperture is located through the body and is sized for the placement of a drill bit therethrough. The first aperture is transverse to the second aperture.

In some arrangements, the second aperture may be orthogonal to a top surface of the body. In other arrangements, the surgical guide structure may include a third aperture parallel to one of the first and second apertures. In still further arrangements, the surgical guide structure may also include an opening through the body, the opening sized and positioned so that when the surgical guide structure is positioned on the first prepared bone surface, the first prepared bone surface and a second prepared bone surface are visible through the opening. In some examples, the opening is partially in between the first and second apertures.

In one embodiment, the present disclosure relates to a surgical guide structure that includes a body with a top surface and a bottom surface. There is at least one aperture through the body and the aperture is sized for the placement of a hole formation instrument therethrough. The at least one aperture has a first size at the bottom surface and a second size at the top surface, the second size being larger than the first size. The surgical guide structure also includes an opening enclosed by the body, the opening sized and positioned so that when the surgical guide structure is positioned on a first resected surface of a bone, the first resected surface and a second resected surface of the bone are visible through the opening.

In some arrangements, the aperture through the body of the surgical guide structure may be defined by an inner wall that includes a first portion having a first slope and a second portion having a second slope different from the first slope. In some examples, the second portion of the inner wall may be orthogonal relative to a planar portion of the top surface of the body. In some examples, the first portion of the inner wall may include a lower part and an upper part, each part having the same first slope, and the lower part and the upper part separated by a step therebetween. In other examples, the first slope is at an angle in a range of 30-35 degrees relative to the top surface of the body.

In some arrangements, the surgical guide structure may include a second aperture through the body of the surgical guide structure that is defined by a second inner wall having a shape different from the first aperture. In some examples, the second inner wall may have a uniform dimension through the body such that the second aperture extends through the body along an axis that is orthogonal relative to the top surface of the body. In other examples, a central axis bisects the body such that the aperture and the second aperture are on a first side of the central axis and a third aperture and a fourth aperture are on a second side of the central axis, the respective apertures being symmetrical about the central axis. In still further examples, the opening may be entirely enclosed by the body, the opening defined by a continuous edge. In these examples, at least a portion of the continuous edge extends along a planar top surface of the body and includes a segment that forms a U-shape directly in between the first aperture and the second aperture.

In some arrangements, the opening of the surgical guide structure may be entirely enclosed by the body, the opening defined by a continuous edge. In these arrangements, at least a portion of the continuous edge extends along a planar top surface of the body and at least a portion extends away from the planar top surface. In some examples, the continuous edge may include a first segment that forms a U-shape along the planar top surface.

In some arrangements, the body of the surgical guide structure may include a central body and an outer portion such that at least part of the bottom surface of the body that corresponds to a prepared bone surface extends along a plane that separates a top surface of the central body from the outer portion. In some examples, the outer portion may be curved and includes a concave surface facing the plane. In some arrangements that include an opening defined by a continuous edge, the portion of the continuous edge that extends away from the planar top surface of the body may extend below the planar top surface. In some arrangements, the surgical guide structure may include a second opening with a shape different than a shape of the first opening.

In one embodiment, the present disclosure relates to a surgical guide structure. The surgical guide structure includes a body configured for placement on a prepared bone surface so that at least part of a bottom surface of the body corresponds to the prepared bone surface when the body is positioned on the bone surface. A first aperture is located through the body and is defined by a first inner wall. The first inner wall is sized for the placement of a hole formation instrument therethrough. Additionally, a second aperture is located through the body and is defined by a second inner wall. The second inner wall is sized for the placement of a hole formation instrument therethrough. The surgical guide structure includes an opening entirely enclosed by the body. The opening is defined by a continuous edge, at least a portion of which extends along a planar top surface of the body and at least a portion of which extends away from the planar top surface. The first inner wall has a first shape and the second inner wall has a second shape, the first shape being different from the second shape.

In some arrangements, the continuous edge of the surgical guide structure may include a first segment that forms a U-shape directly in between the first aperture and the second aperture. In some arrangements, the opening of the surgical guide structure may be sized and positioned so that when the surgical guide structure is positioned on the first prepared bone surface, the first prepared bone surface and a second prepared bone surface are visible through the opening. In some examples, the body includes a central body and an outer portion. In these examples, the at least part of a bottom surface of the body that corresponds to the prepared bone surface extends along a plane that separates a top surface of the central body from the outer portion. In other examples, the outer portion is curved and includes a concave surface facing the plane.

In one embodiment, the present disclosure relates to a kit that includes at least one trial implant and at least one surgical guide. The at least one trial implant includes a main body with a convex top surface and an outer portion secured to the main body so that an opening is defined by a space between the main body and the outer portion. The at least one surgical guide structure includes an opening sized to expose more than a single resected surface of a bone when positioned on a resected surface of the bone.

In some arrangements, the trial implant of the kit may include a second opening smaller than the first opening. In some examples, the trial implant may include a third opening in between the first and second openings. In other arrangements, the surgical guide structure of the kit may include at least one aperture sized for placement of a drill bit therethrough. In some examples, the aperture through the surgical guide structure may be transverse relative to a top surface of the body. In other examples, the kit may also include a surgical guide structure with a second aperture that is transverse to the first aperture.

In one embodiment, the present disclosure relates to a method of preparing a bone for placement of an implant. The steps of the method involve: performing a first resection of a bone to create a first surface; performing a second resection of the bone to create a second surface so that the second surface abuts the first surface; placing a surgical guide structure on the first surface so that at least part of the surgical guide structure is flush with the first surface; and viewing the first and second surfaces through an opening in the surgical guide structure. The surgical guide structure used in the method includes an aperture adapted for receiving a drill bit.

In some arrangements, the method may also include placing a drill through the aperture in the surgical guide structure. The aperture may be shaped to accommodate a range of drill trajectories at acute angles relative to the first surface. In some examples, the method may also include viewing a third surface of the bone through a second opening in the surgical guide structure.

In some arrangements, the method may include removing the surgical drill guide structure and placing a trial implant on the first surface of the bone, the trial implant sized to correspond to a prosthetic implant. In some examples, the method may include viewing the second surface through an opening in the trial implant while at least a portion of a bottom surface of the trial implant is flush with the first surface of the bone. In other examples, the method may include viewing a third surface of the bone through a second opening in the trial implant while at least a portion of a bottom surface of the trial implant is flush with the first surface of the bone.

In one embodiment, the present disclosure relates to a method of preparing a bone for placement of an implant. The method includes placing a trial implant on a first surface of a resected bone so that at least a portion of the trial implant corresponds to the first surface; aligning the trial implant with an intended implant position on the first surface of the resected bone so that the trial implant is seated on the bone; viewing the first surface, a second surface, a third surface, and a fourth surface of the resected bone through an opening in the trial implant to evaluate seating and alignment of the trial implant on the bone; and rotating the bone relative to a second bone on an opposite side of a joint therebetween to evaluate an articulating surface of the trial implant.

In some arrangements, the aligning step may include positioning a protrusion of the trial implant with a formed bone hole in the first surface such that the protrusion engages with the hole. In some examples, the method may also involve removing the trial implant from the resected bone and positioning an implant relative to the first surface of the bone so that upon positioning a protrusion of the implant into the formed bone hole, at least a portion of the protrusion is positioned in the formed bone hole and at least a portion of the protrusion is positioned in the bone adjacent to the bone hole. In some examples, the protrusion may be orthogonal to the prepared surface of the bone as it enters the formed bone hole. In further examples, the method may also involve placing a trial bearing in a joint space abutting the trial implant.

In one embodiment, the present disclosure relates to a joint replacement system that includes a surgical guide structure and an implant. The surgical guide structure includes a body and at least one aperture through the body, the at least one aperture sized for placement of a drill bit therethrough and adapted to form a bone hole in a bone. The implant includes a protrusion adapted to secure the implant to the bone.

In some arrangements, the aperture through the body of the surgical guide structure may be transverse relative to a prepared surface of the bone. Additionally, the formed bone hole may be transverse to the prepared surface of the bone. In some examples, the protrusion of the implant may be transverse relative to the formed bone hole and may be positioned in the bone hole such that, upon final positioning of the implant relative to the prepared surface of the bone, at least a portion of the protrusion is positioned in the bone hole and at least a portion of the protrusion is positioned in the bone adjacent to the bone hole. In other examples, the protrusion may be orthogonal to the prepared surface of the bone.

In one embodiment, the present disclosure relates to a template that includes a shaft and a template frame for use on a resected bone surface. The shaft includes an engagement feature therein and the template frame is attached to the shaft. A first end of the template frame abuts the shaft and a second end of the template frame is remote from the shaft. The template frame defines a planar surface that extends between the first end and the second end. The template frame includes an outer perimeter and an inner perimeter. The inner perimeter forms an opening through the template frame. The template frame may have an outer width extending between opposite sides of the outer perimeter and an inner width extending between opposite sides of the inner perimeter. The outer width and the inner width are measured at a single location between the first end and the second end of the template frame and the outer width may be less than two times the inner width. The outer perimeter of the template frame may be shaped to correspond to an outer edge of a resected talar bone. Further, the template frame may include at least one protrusion thereon that extends transverse to a length of the shaft. The shaft and the template frame may be a combined, monolithic structure.

In one embodiment, the present disclosure relates to a template for use on a resected bone surface. The template includes a shaft and a template frame. The template frame is attached to the shaft. A first end of the template frame abuts the shaft and a second end of the template frame is remote from the shaft. The template frame defines a planar surface extending between the first end and the second end and includes an inner perimeter forming an opening through the template frame.

In some arrangements, the template frame may have an outer width extending between opposite sides of an outer perimeter of the template frame and an inner width extending between opposite sides of the inner perimeter. The outer width and the inner width may be measured at the same location between the first end and the second end of the template frame. The outer width may be less than two times the inner width. In some arrangements, the inner perimeter of the template defines a first cross-sectional area and an outer perimeter of the template defines a second cross-sectional area. The second cross-sectional area may be less than two times the first cross-sectional area. In some arrangements, the template frame may include an outer perimeter shaped to correspond to an outer edge of a resected talar bone. In other arrangements, the template frame may include at least one protrusion thereon extending transverse to a length of the shaft. In further arrangements, the shaft and the template frame may be monolithic.

In some arrangements, the shaft of the template may include an engagement feature therein. In certain examples, a system may include the template and a drill guide that includes an engagement feature complementary to the engagement feature on the shaft. In some examples, the drill guide also includes an opening mount at an end of the drill guide opposite the engagement feature. The opening mount may be adapted to receive a datum pin. In other examples, the drill guide may be mountable on the template through engagement of the respective engagement features so that one end of the drill guide is positioned over a center of the opening in the template.

In one embodiment, the present disclosure relates to a method that includes: placing a template frame of a template onto a resected bone surface in a joint of a body; comparing an outer perimeter of the template frame with an outer perimeter of the resected bone surface to determine whether the respective dimensions correspond; placing a drill guide onto the template so that an end of the drill guide is positioned in an opening through the template frame; and drilling a datum pin into the resected bone surface through the drill guide while the template frame remains positioned on the resected bone surface.

In some arrangements, the method may include placing a second template onto the resected bone surface in the joint when the outer perimeter of the template does not correspond to the outer perimeter of the resected bone surface. In other arrangements, the method may include placing the drill guide onto the template so that a first engagement feature on the drill guide engages a second engagement feature on a shaft of the template.

In one embodiment, the present disclosure relates to a joint space evaluator that includes a main body with a recessed portion and a pivoting member. The pivoting member is attached to the recessed portion of the main body by an element extending through a portion of the recessed portion and a portion of the pivoting member. The pivoting member pivots about an axis passing through a length of the element. The main body includes a first indicator and the pivoting member includes a second indicator, the first and second indicators being in alignment when an outward facing surface of pivoting member and an opposing outward facing surface of the recessed portion are parallel and the first and second indicators being out of alignment when the outward facing surface of the pivoting member and the opposing outward facing surface of the recessed portion are not in parallel.

In some arrangements, at least a portion of an inward facing surface of the pivoting member of the joint space evaluator may be spaced apart from an opposite inward facing surface of the recessed portion. In other arrangements, the pivoting member may include one of a convex or a concave surface along its length and the recessed portion may include the other of the convex or the concave surface along its length. In this arrangement, the convex and the concave surfaces are flush with one another irrespective of a position of the pivoting member relative to the recessed portion. In some arrangements, a method of using the joint space evaluator may include inserting the joint space evaluator in between two resected bone surfaces of a joint in a body; viewing a position of the first indicator relative to the second indicator to determine whether the first indicator is aligned with the second indicator; and conducting tissue balancing on the medial or lateral side of the joint when the second indicator is out of alignment with the first indicator until the second indicator is aligned with the first indicator.

BRIEF DESCRIPTION OF THE DRAWINGS

A more complete appreciation of the subject matter of the present disclosure and of the various advantages thereof can be realized by reference to the following detailed description in which reference is made to the accompanying drawings in which:

FIG. 31 is a top view of a template frame of the post talar cut template of FIG. 25 positioned on a resected talus according to one embodiment of a method of the present disclosure;

FIGS. 32 and 33 are top and perspective views, respectively, of a drill guide attached onto the post talar cut template according to further steps of the method;

DETAILED DESCRIPTION

As used herein when referring to bones or other parts of the body, the term "proximal" means close to the heart and the term "distal" means more distant from the heart. The term "inferior" means toward the feet and the term "superior" means toward the head. The term "anterior" means toward the front part or the face and the term "posterior" means toward the back of the body. The term "medial" means toward the midline of the body and the term "lateral" means away from the midline of the body.

The present disclosure relates to devices, systems, kits and methods used in joint repair surgeries. In particular, the embodiments relate to structures and associated uses of such structures in preparation for implant placement, including placement of a prosthetic implant on a resected talar surface in the foot. Although the embodiments are described with particular application to the ankle joint, it is contemplated that the teachings embodied by the described structures and methods may be incorporated into devices, systems, kits and methods used in other areas of the body. For example, the teachings of the present disclosure may be used to improve upon hip, knee, elbow, shoulder and smaller joint (such as wrist, finger, or toe) replacement surgeries.

Trial Implant and Drill Guide

In one aspect, the present disclosure relates to a trial talar implant, or trial implant, with openings. The openings function as windows through the trial implant structure so that surfaces under the trial implant are visible through the openings. The trial implant is suited for the measurement of talar resections, i.e., cuts, and is shaped accordingly. Such measurement aids in determining whether the resections are satisfactory or whether further cutting of the talus is necessary. One embodiment of a trial implant is shown in FIGS. 1-4. Trial implant 100 includes a central portion 110 and outer portions 120, 130.

Figure 1:
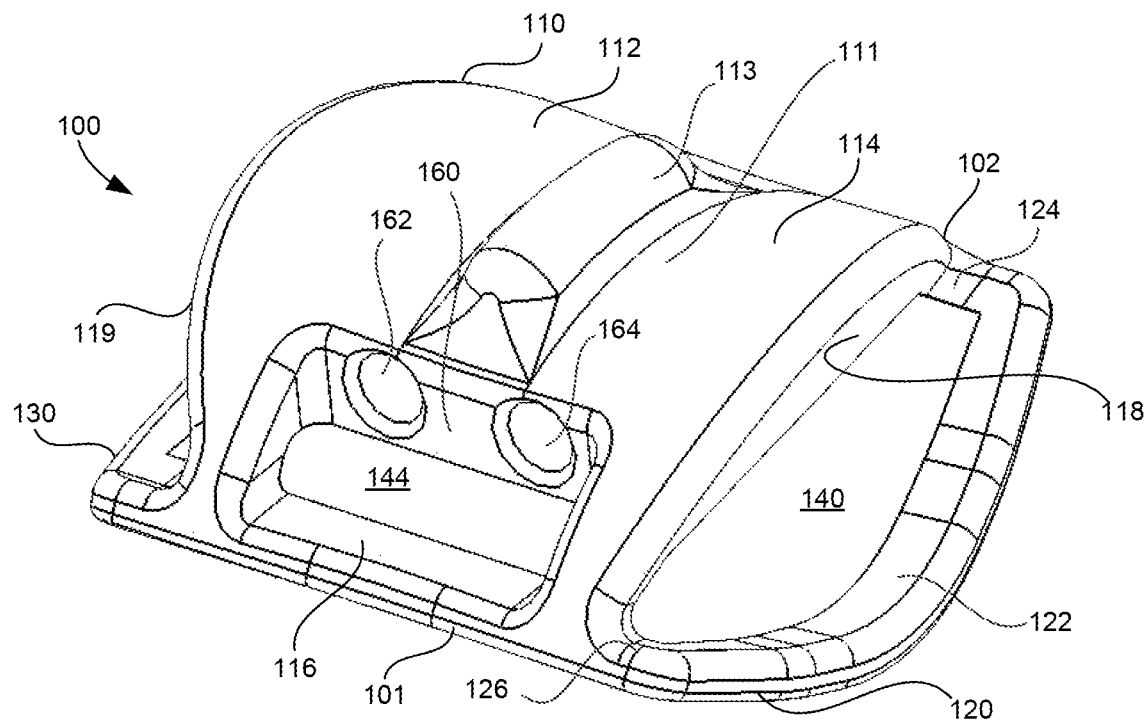
FIG. 1 is a perspective view of a trial implant according to one embodiment of the present disclosure.
Figure 2:
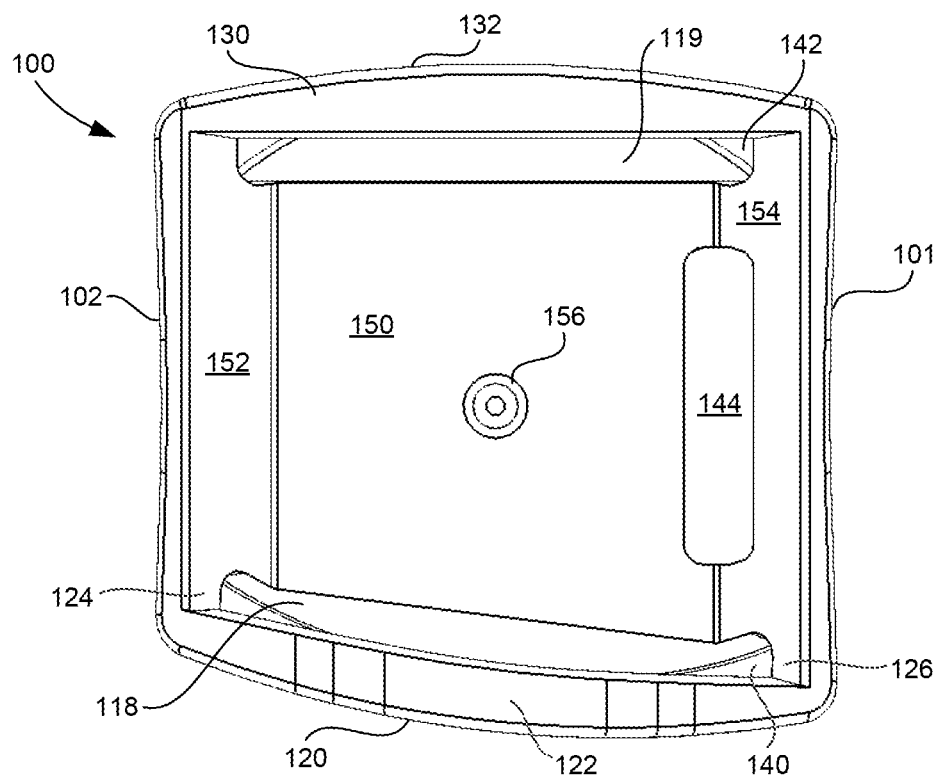
FIG. 2 is a bottom view of the trial implant of FIG. 1.
Figure 4:
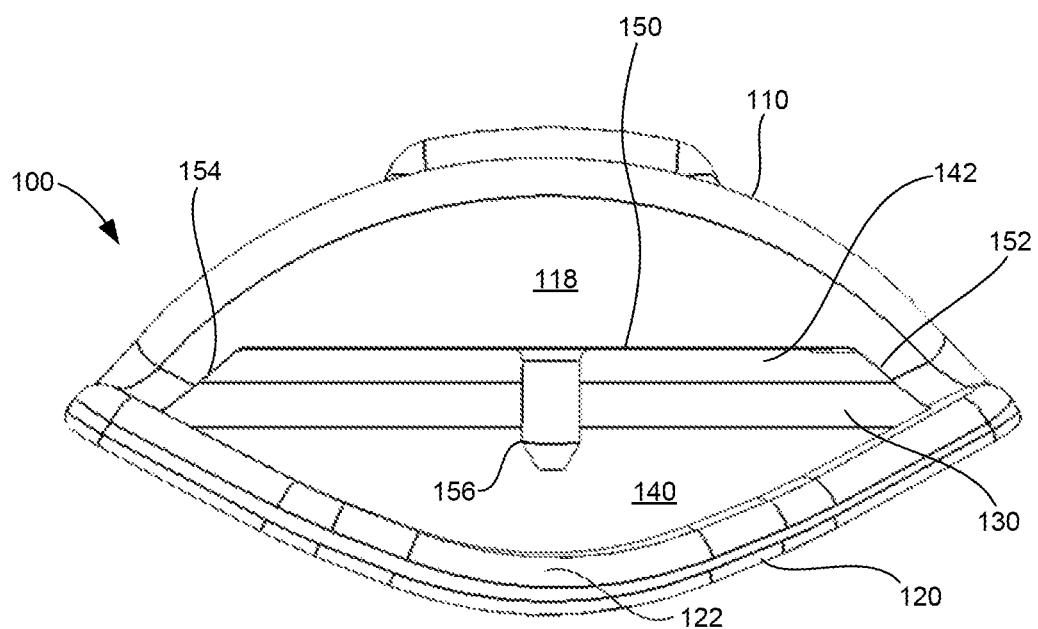
FIG. 4 is a side view of the trial implant of FIG. 1.
Figure 12:
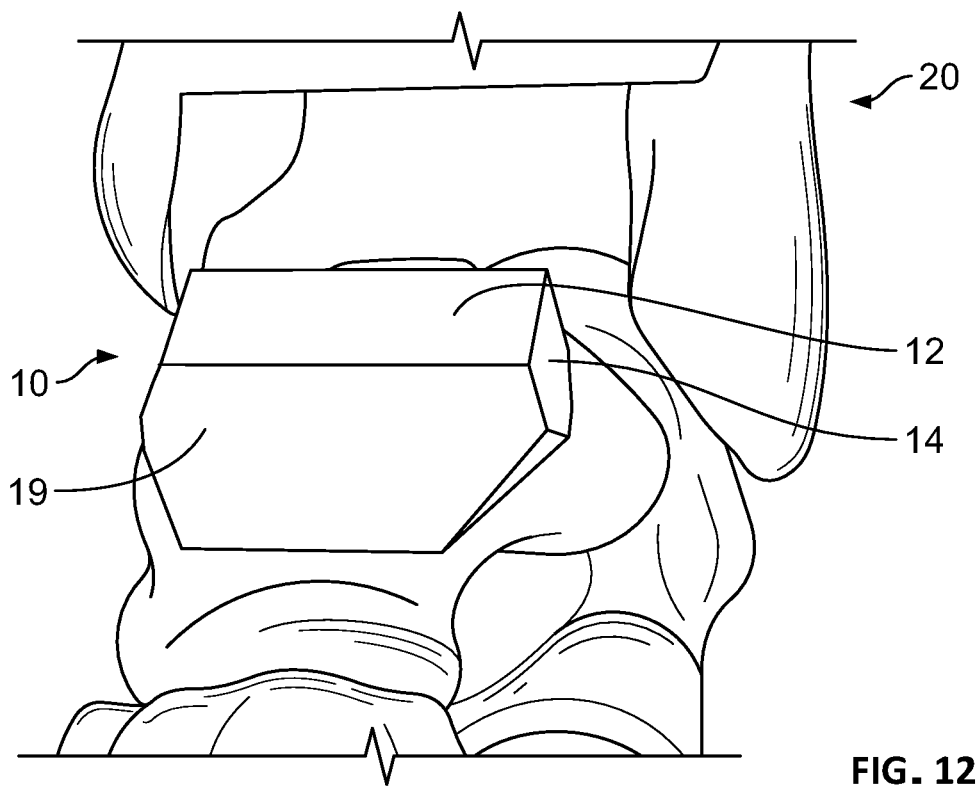
FIG. 12 illustrates an ankle joint prepared for placement of implants according to one embodiment of a method of the present disclosure.
Figure 17:
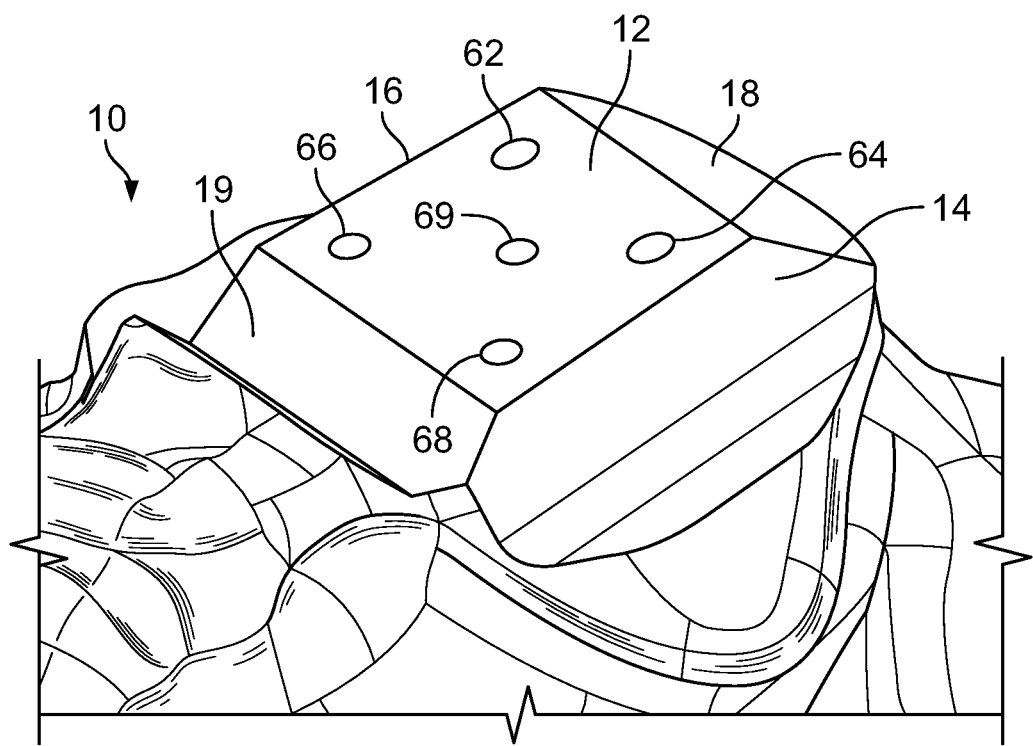
Figure 21:
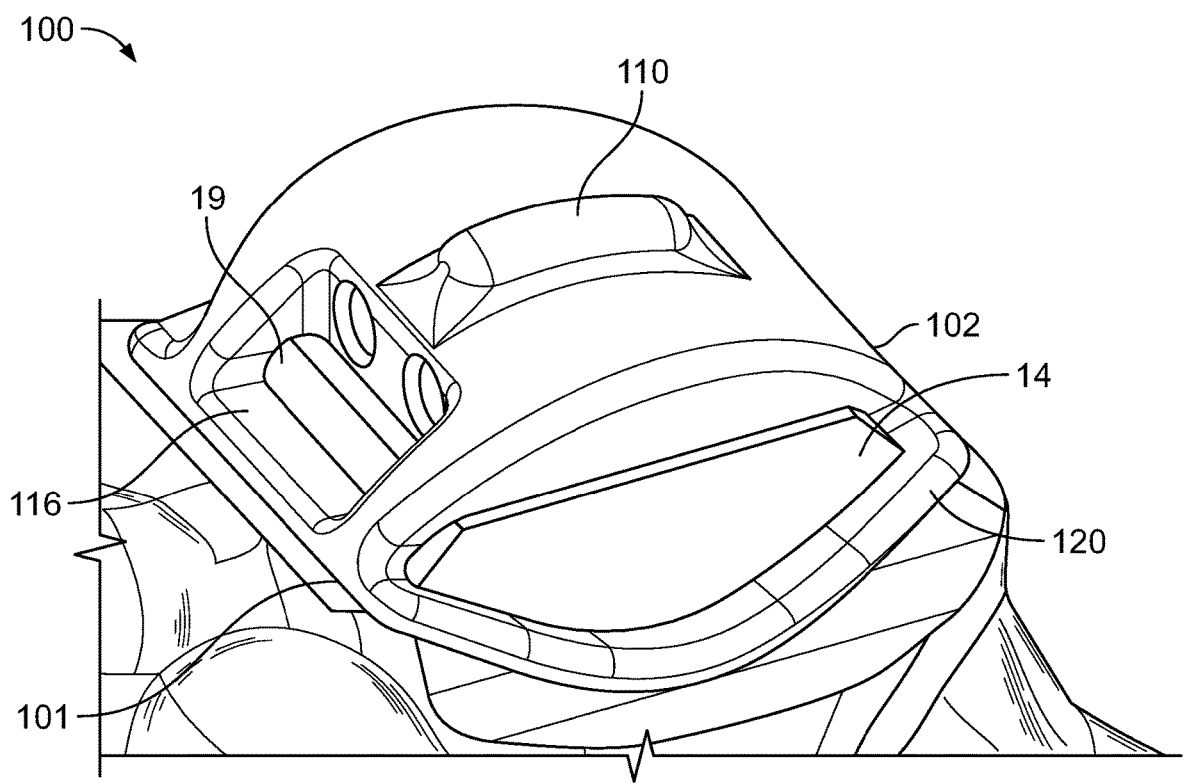
Figure 22:
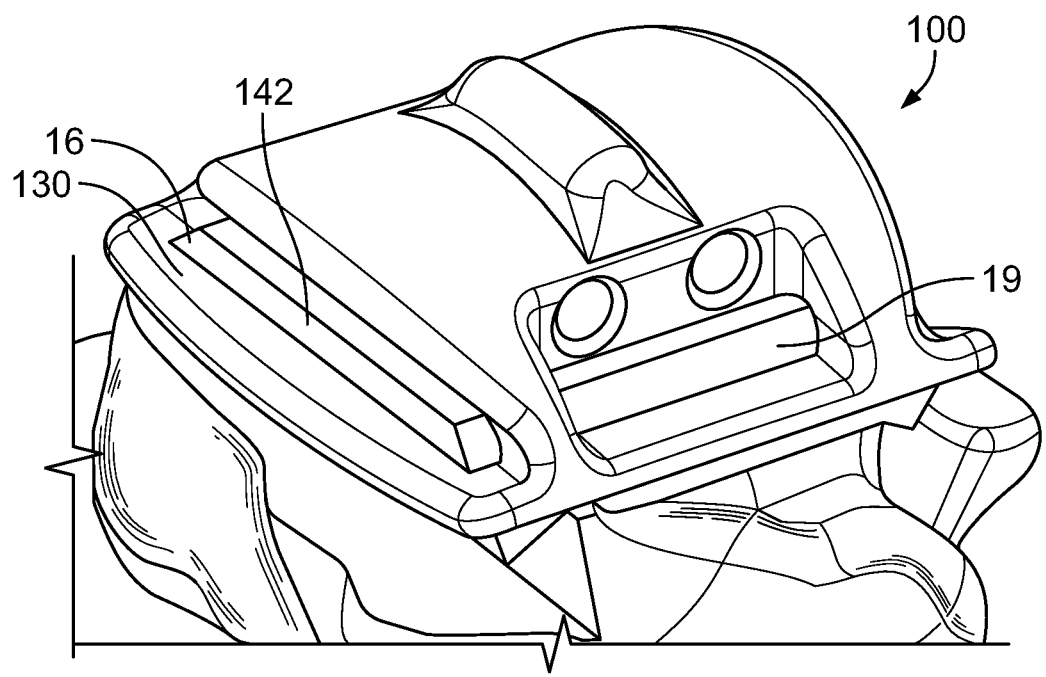

Central portion 110, as best shown in FIG. 1, includes a top face 111, which in this embodiment defines top surfaces 112, 114 separated by a ridge 113. Each top surface 112, 114 is convex in shape and extends between first and second ends 101, 102 of the trial implant. Trial implant 100 is sized to correspond to a talar implant size. In this manner, convex top surfaces 112, 114 have a radius and other surface features dimensioned to predict how well the actual permanent (long-term) prosthetic implant, when secured to the talus, will be able to articulate and otherwise function within the joint. In this manner, upper surfaces represent an articulating surface. This articulating surface is shaped to be the same as an articulating surface for a permanent implant of the same size. Top surfaces 112, 114 are generally unobstructed although an opening 144 exists near first end 101, as shown in FIGS. 1 and 2. Bottom surface 150 of trial implant 100 is generally planar as shown in FIG. 4 while bottom surfaces 152, 154 taper toward first and second ends 101, 102, such as is shown in FIG. 4. Bottom surfaces 150, 152, 154 are shaped to correspond to resected surfaces 12, 18, 19, as shown in FIGS. 12 and 17. When trial implant 100 is positioned on surfaces 12, 18, 19, ends 101 and 102 will contact or otherwise be adjacent to surfaces 19 and 18, respectively, as shown in FIG. 21. Extending from a central location on bottom surface 150 is a protrusion in the form of a post 156. The post is configured for placement in a hole through the top resected surface of the talus to secure trial implant 100 to bone. When trial implant 100 is secured to talus 10, as best shown in FIGS. 21 and 22, an inner surface of outer portion 120 corresponds to bone surface 14 while an inner surface of outer portion 130 corresponds to bone surface 16.

Figure 3:
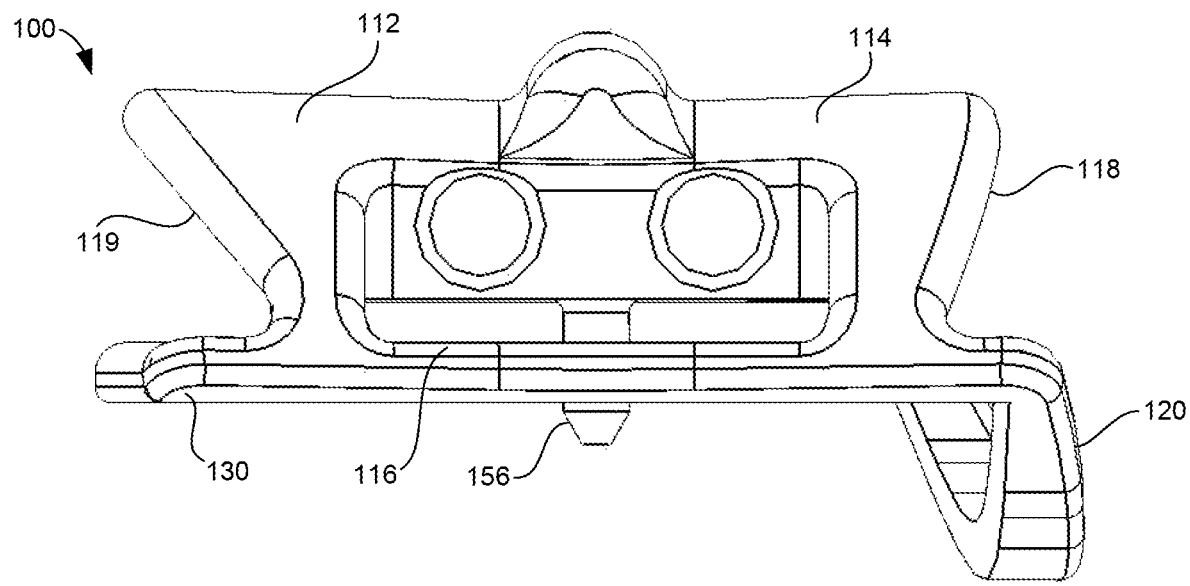
FIG. 3 is an end view of the trial implant of FIG. 1.

Bridging a separation between top surfaces 112, 114 and bottom surfaces 150, 152, 154 are side surfaces 118, 119. Both side surfaces 118, 119 have angled surfaces moving inward from top surfaces 112, 114 toward bottom surfaces 150, 152, 154. As best shown in FIG. 3, an angle of surface 118 is shallower than an angle of surface 119 when the angle is measured relative to an axis through post 156. In this manner, surface 118 is closer to being perpendicular to bottom surface 150 when compared to surface 119. Each of side surfaces 118, 119 has a depth and angle to correspond and otherwise mimic an implant size. In this manner, trial implant 100 is configured so that when it is positioned on a bone, e.g., a talus, it provides visual cues as to whether the implant would impinge on adjacent bodily structures or other implant components on the medial or lateral side of the implant. Due to the angle of side surfaces 118, 119, a combined width of top surfaces 112, 114 is greater than a width of bottom surface 150. Also, each side surface 118, 119 has a lesser dimension extending between bottom and top surfaces than the width of either top 112, 114 or bottom 150 surfaces. The unique geometry defined in part by side surfaces 118, 119 provides a large area articulation surface on the top of the trial while at the same time also leaves space for openings 140, 142 sufficiently sized so that multiple resected bone surfaces may be viewed through such openings when trial implant 100 is seated on a bone.

As noted above, opening 144 extends through top surfaces 112, 114 adjacent to first end 101, as shown in FIG. 1. When trial implant 100 is positioned on talar bone 10, opening 144 allows for visualization of resected anterior surface 19, as shown in FIG. 21. Trial implant 100 also includes a bar 116 extending across first end 101 between outer portions 120, 130. Opening 144 is defined on one side by bar 116 and on others by top surfaces 112, 114, as shown in FIG. 1. Within opening 144 is a surface 160, as best shown in FIG. 1. Surface 160 includes openings 162, 164, which are configured to allow engagement by a tool such as a forceps or for evaluating a position of trial implant 100 relative to the surrounding anatomy.

Trial implant 100 also includes outer portions 120, 130. Outer portion 120 and outer portion 130 are different from one another. Outer portion 120 is a curved shape as shown in FIGS. 1, 3 and 4, and extends from first end 101 to second end 102. Outer portion 120 includes lateral branches 124, 126 connecting a longitudinal segment of outer portion 120 with central portion 110. Positioning of lateral branches 124, 126 is such that outer portion 120 lies entirely on one side of a plane through side surface 118. The curve of the longitudinal segment of outer portion 120 is outward relative to side surface 118 and bottom surface 150 so that an apex 122 of outer portion 120 roughly represents a location of maximum width of opening 140, as best shown in FIGS. 1 and 4. As depicted, outer portion 120 is monolithic with central portion 110 and extends from ends 101 and 102 of central portion 110. A space between side surface 118 and outer portion 120 defines opening 140. Opening 140 extends between ends 101 and 102. In particular, opening 140 widens from end 101 toward apex 122 then narrows from apex 122 toward end 102.

Outer portion 130, as with outer portion 120, extends from first end 101 to second end 102 and includes lateral branches that connect a longitudinal segment with central portion 110. However, although an outer edge 132 of outer portion 130 is curved, as shown in FIG. 2, a longitudinal axis through the longitudinal segment of outer portion 130 is generally linear and of a constant depth relative to bottom surface 150, unlike the longitudinal segment of outer surface 130. The constant depth of outer portion 130 is visible in FIGS. 3-4, for example. Between outer portion 130 and side surface 119 is opening 142. Opening 142 is smaller than opening 140 and is generally uniform in width between ends 101 and 102, as can be seen from FIGS. 2 and 22. In the depicted embodiment, one functional difference between opening 140 and 142 when trial implant 100 is secured on talus 10 is that a larger area of resected surface 14 is visible through opening 140 when compared with an area of resected surface 16 visible through opening 142.

Figure 5:
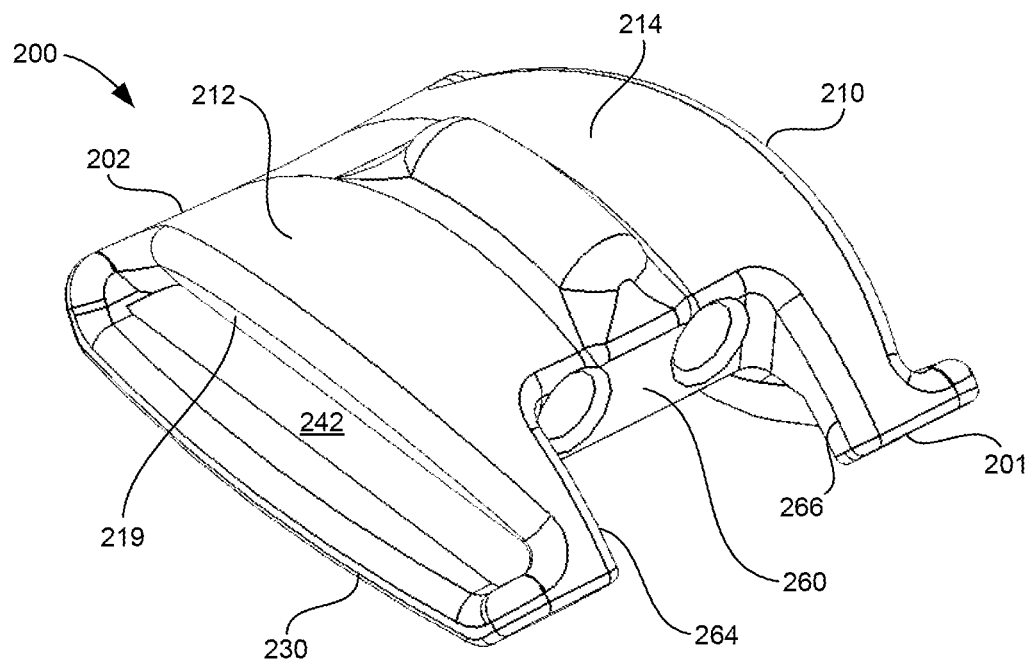
FIG. 5 is a perspective view of a small trial implant according to one embodiment of the present disclosure.
Figure 6:
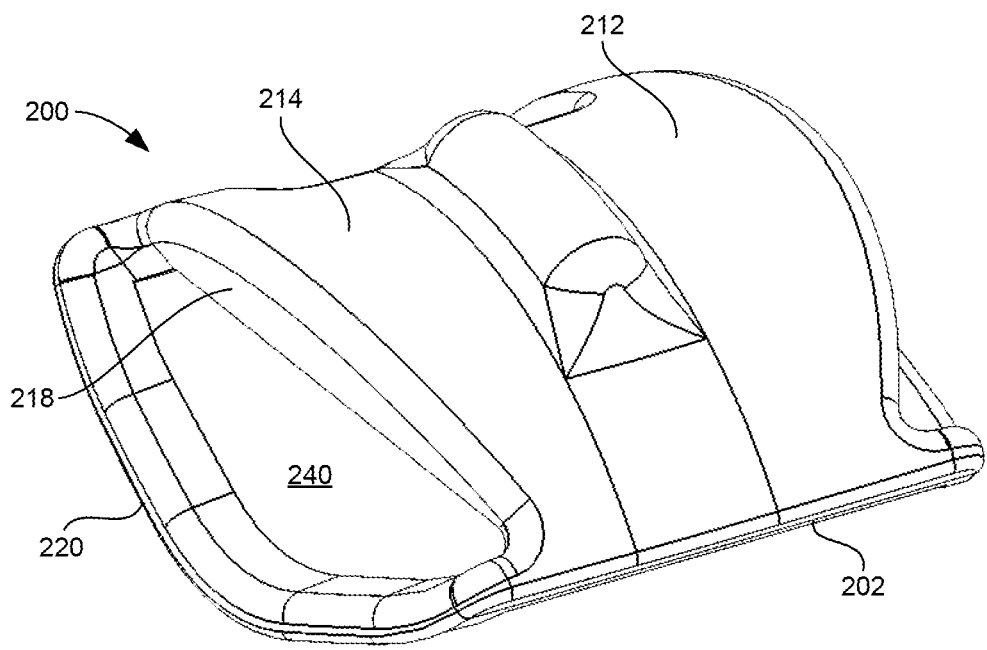
FIG. 6 is another perspective view of the small trial implant shown in FIG. 5.

In another embodiment, a trial implant designed for implantation in the joint of a patient with a small talus is contemplated, as shown in FIGS. 5 and 6. The principles surrounding this embodiment follow those of the embodiment described above, and unless otherwise stated, like reference numerals refer to like elements. For example, top surfaces 212, 214 are equivalent to top surfaces 112, 114 and have the same diameter. One difference between trial implant 100 and trial implant 200 is that a depth of trial implant 200 is less than that of trial implant 100. To reduce the depth of the trial implant, bottom portions including the bar and portions of outer portions are removed, while maintaining the bearing surfaces needed on the top of the trial. For example, as visible in FIG. 5, trial implant 200 does not include a bar at its first end 201, unlike trial implant 100. Trial implant 200 includes a central portion 210 and outer portions 220, 230, as in the embodiment of FIG. 1. Also similar are openings 240, 242 between outer portion 220 and central body portion 210 and between outer portion 230 and central body portion 210, respectively. However, as noted above, at first end 201 of trial implant 200, a recessed area defined by walls 260, 264, 266 replaces a closed opening through the top surfaces.

The trial implant of the present disclosure may be varied in many ways other than the embodiments discussed above. For example, the shape of each opening/window may vary from that shown in the depicted embodiments. Similarly, the size of each window may be larger or smaller than that depicted. In some examples, the window may be sized and positioned so that one, two, three, or four resected surfaces are visible when the trial is positioned on a resected talus. The number of windows may also be varied. For example, a trial implant may include one, two, three, four, or more windows. In further examples, alternatively or in addition to the window on the anterior side of the trial, a window may be included on the posterior side through the convex surface of the trial. In other examples, sloped side surfaces between the top surface and the bottom surface of the trial implant may vary from those shown in the depicted embodiment. An angle of either or both may be less or greater than that shown, and may vary in unison or independently. A length of either side surface may also vary.

Protrusions, or spikes, may be absent from the bottom surface of the trial or may be included in a quantity of one or more. A shape of each protrusion may vary from that shown in the depicted embodiment and where two or more protrusions extend from the bottom surface, each protrusion may have a shape independent of the other. Further, various securement mechanisms as known in the art, other than the aforementioned spike or protrusion, may be used to releasably secure the trial implant to bone when in position for implant placement preparation. A geometric shape of the bottom surface of the trial implant may be altered from the shape defined by bottom surfaces 150, 152, 154 of the embodiment depicted in FIGS. 1-4. In this manner, there may be four or more bottom surfaces. The outer portions of the trial may also have geometry that varies from the depicted embodiments. For example, a singular outer portion may define a perimeter of the trial implant, extending around the central portion and separated from it by openings. In other examples, the trial implant includes two outer portions that may both be curved or parallel to a bottom surface of the trial. Where an outer portion is curved, the radius may vary or be constant, and may be any radius feasible within an available space. Each outer portion may be varied with respect to the other. A cross sectional shape of the outer portions may also vary based on considerations such as space needed for use and material choice, among other factors. In some examples, the trial implant includes a single outer portion. In any of the above embodiments and examples, the structure of the trial implant may be monolithic or modular. Although described in the context of the ankle, the trial implant may also be shaped for seating on resected bone surfaces in other joints. In such cases, the trial implant may include windows and/or recesses so that two, three, four, five, or more resected surfaces are visible. In any of the above embodiments, stainless steel may be used to manufacture the trial. In one example, manufacture of the trial may be accomplished using machining techniques. Other materials and manufacturing techniques one of ordinary skill would consider using for trial implants are also contemplated.

The trial may be manufactured in known ways and shipped to operators for use in a patient. Alternatively, the trial may be formed as a custom trial implant at the surgical facility using an Additive Layer Manufacturing (ALM) fabrication process such as selective laser sintering (SLS), selective laser melting (SLM), or electron beam melting (EBM), as disclosed in U.S. Pat. Nos. 7,537,664; 8,728,387; 9,180,010; and 9,456,901, the disclosures of which are hereby incorporated by reference in their entireties herein. Other appropriate 3D printing technologies known to those skilled in the art, such as fused deposition modeling, may also be used. When employing powder-bed based technologies for the above processes, articles are produced in layer-wise fashion according to a predetermined digital model of such articles by heating, e.g., using a laser or an electron beam, multiple layers of powder, which preferably may be a metallic powder, that are dispensed one layer at a time. The powder is sintered in the case of SLS technology and melted in the case of SLM technology, by the application of laser energy that is directed in raster-scan fashion to portions of the powder layer corresponding to a cross section of the article. After the sintering or melting of the powder on one particular layer, an additional layer of powder is dispensed, and the process repeated, with sintering or melting taking place between the current layer and the previously laid layers until the article is complete. The powder layers similarly may be heated with EBM technology. Additive manufacturing techniques such as the ALM processes described above may be employed to form the trial implant and any other components, as applicable. In some instances, materials for one layer may be different than the materials for successive layers. The above described custom trial implant can be formed based on data of the particular surgical site, such as the shape of the prepared talus bone.

Figure 7:
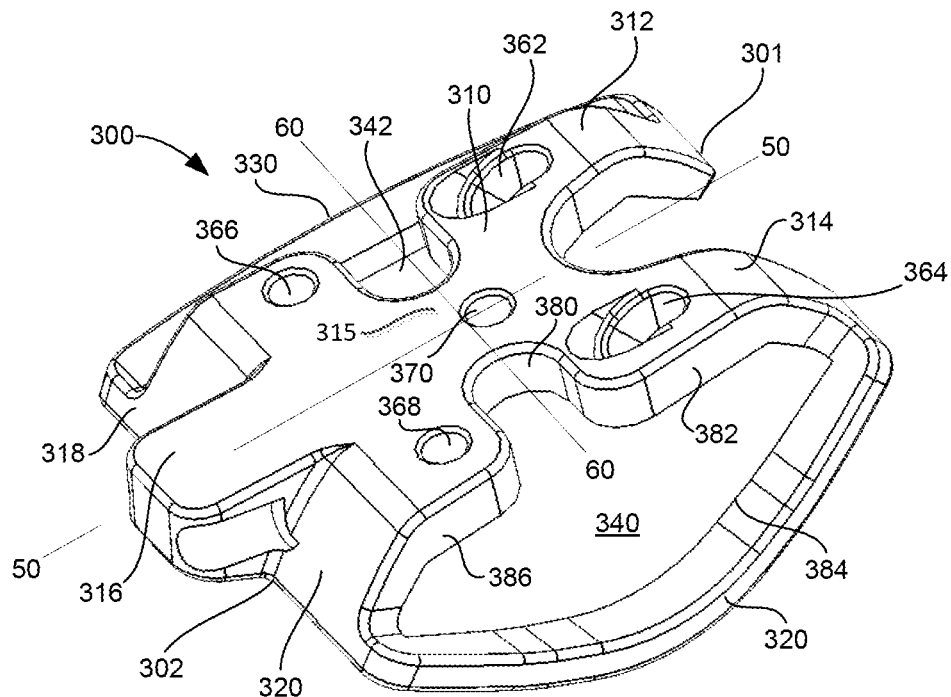
FIG. 7 is a perspective view of a surgical guide structure according to one embodiment of the present disclosure.
Figure 8:
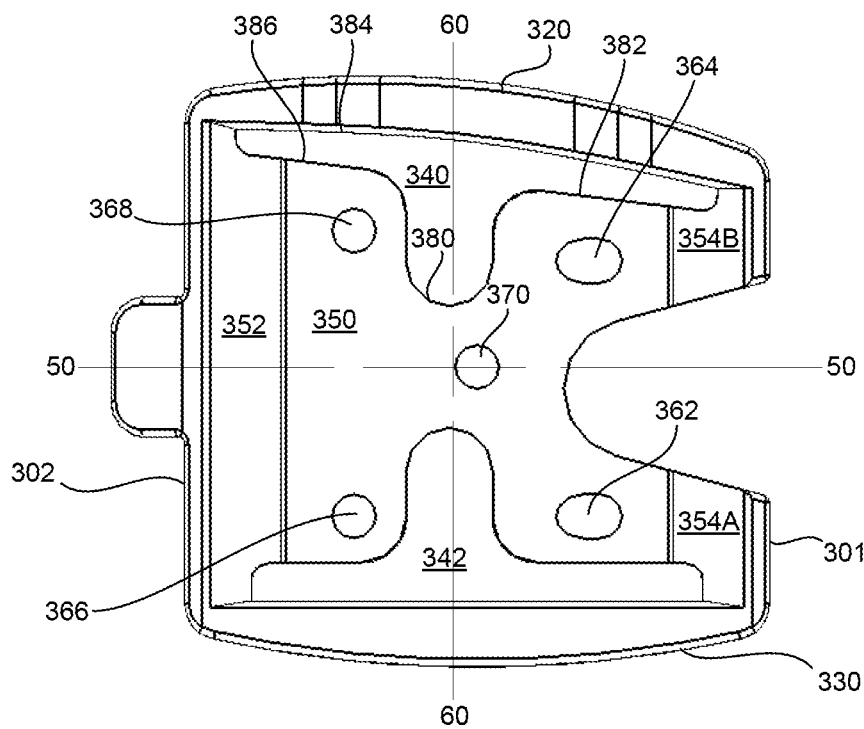
FIG. 8 is a bottom view of the surgical guide structure of FIG. 7.

In another aspect, the present disclosure relates to a surgical guide structure configured for use in identifying locations on a bone surface to create and otherwise form holes sized for the insertion of protrusions, posts, spikes, or other securement mechanism of a talar implant. In one embodiment, a surgical guide structure is as shown in FIG. 7. Surgical guide structure 300 includes a main body with a principal top surface 310 having forked extensions 312, 314 defining a gap therebetween at a first end 301 and a central extension 316 at a second end 302. Central extension 316 protrudes from outer portions 318, 320 and includes medial and lateral concave surfaces 317. These concave surfaces 317 are shaped to render it easier to use a forceps to engage and hold onto guide structure 300. In a central region approximately midway between first and second ends 301, 302, top surface 310 has a neck 315 as shown in FIGS. 7 and 8. An axis 50 extends longitudinally between first and second ends 301, 302 dividing structure 300 into approximately equal sections, as best shown in FIG. 8. One section includes an entirety of outer portion 320 while the other includes an entirety of outer portion 330. Passing through top surface are five apertures 362, 364, 366, 368 and 370. Apertures 362, 364 are defined by varying angle perimeter walls, described in greater detail below, while apertures 366, 368 define a cylindrical path through the surgical guide structure. Aperture 370 is centrally located on the guide structure on axis 50 and is adjacent to neck 315 of top surface 310, as shown in FIGS. 7 and 8. When viewed on each side of axis 50 between first and second ends 301, 302, these sections of the surgical guide structure are nearly but not quite symmetrical. In particular, the section having outer portion 320 tapers outward from first end 301 toward second end 302 so that it is much wider at end 302. Additionally, outer portion 320 itself is of a different shape than outer portion 330. These and other features of the structure are described in greater detail below.

Outer portions 320, 330, as noted above, are on lateral sides of surgical guide structure 300 and extend generally along a length of the body. Outer portion 320 is curved in a concave manner relative to both surface 310 and side surfaces 382, 386 such that an approximate midway point of outer portion 320 is furthest from top surface 310 compared to other locations on outer portion 320. This curve is seen from different perspectives in FIGS. 7-10. Surfaces 380, 382, 384, 386 of the guide structure define an opening 340, as best shown in FIG. 7. Surface 384 is an inner edge part of outer portion 320 while the remaining surfaces define an edge of the main body of structure 300. From first end 301, surface 382 tapers away from axis 50 toward second end 302 and is generally linear. Approximately midway between first and second ends 301, 302, surface 382 transitions to U-shaped surface 380, which extends inward toward axis 50 and includes a radius centered on axis 60, as shown in FIGS. 7 and 8. U-shaped surface is sized and positioned so that it lies in between apertures 364 and 368. Continuing toward second end 302, surface 380 transitions to surface 386, which is on approximately the same plane as surface 382, as best shown in FIG. 8. In this manner, surface 386 tapers away from axis 50 toward second end 302. Connecting surfaces 382 and 386 is surface 384 on a side of outer portion 320. Surface 384 has a large radius, also shown in FIG. 8, and tapers away from axis 50 from first end 301 to second end 302. Opening 340 is defined by surfaces 380, 382, 384, 386, which form a perimeter around opening 340.

Figure 9:
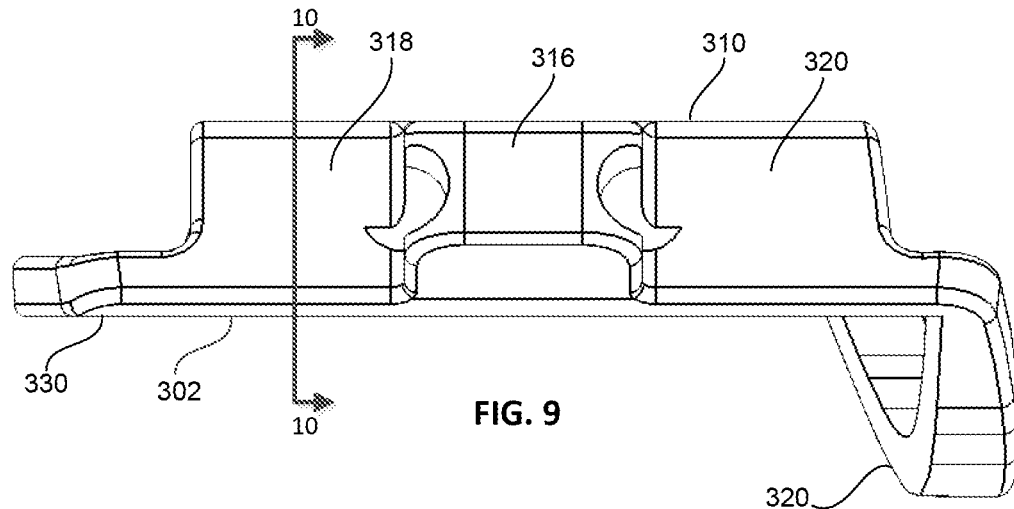
FIG. 9 is an end view of the surgical guide structure of FIG. 7.

On an opposite side of axis 50 lies outer portion 330 separated from the main body of structure 300 by opening 342. Unlike outer portion 320, outer portion 330 is of a generally linear shape and does not curve out of a plane parallel to top surface. This difference between outer portions 320, 330 is best shown in FIG. 9. Returning to opening 342, surfaces of structure 300 that define opening 342 are generally parallel to axis 50, as best shown in FIG. 8. However, a U-shaped surface extends inward toward axis 50 opposite surface 380 near the midway location on the length of surgical guide structure 300, defining a portion of neck 315 on surface 310.

Figure 10:
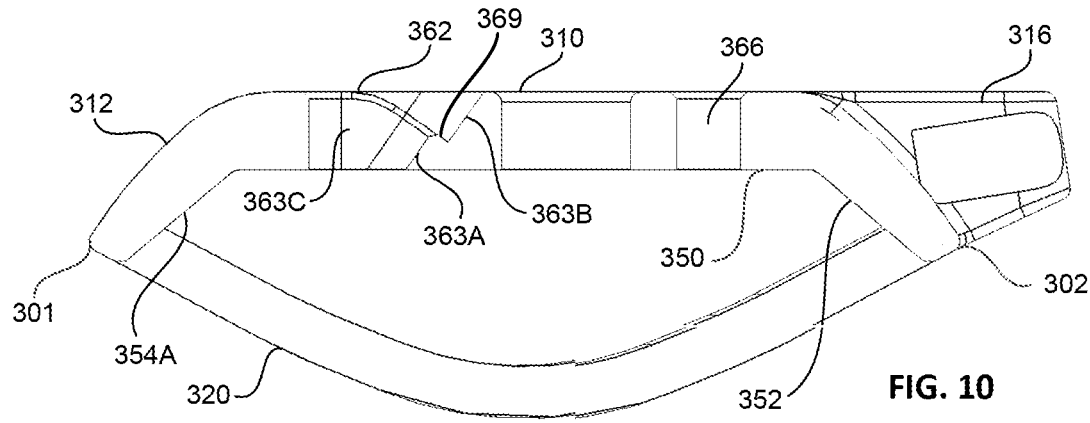
FIG. 10 is a sectional view of the surgical guide structure of FIG. 7.

A central bottom surface 350 of surgical guide structure 300 is planar and parallel to top surface 310. Apertures 362, 364, 366, 368, 370 extend between top surface 310 and bottom surface 350. Adjacent to first end 301 are bottom surfaces 354A-B, which taper away from the plane through top surface 310. Similarly, adjacent to second end 302, bottom surface 352 tapers away from the plane through top surface 310. An angle of each surface relative to bottom surface 350 is best shown in FIG. 10.

Figure 11:
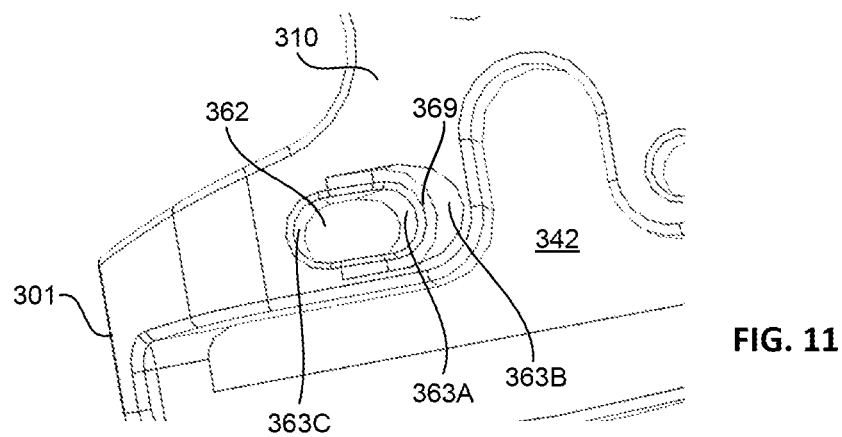
FIG. 11 is a close up top view of the surgical guide structure of FIG. 7.
Figure 13:
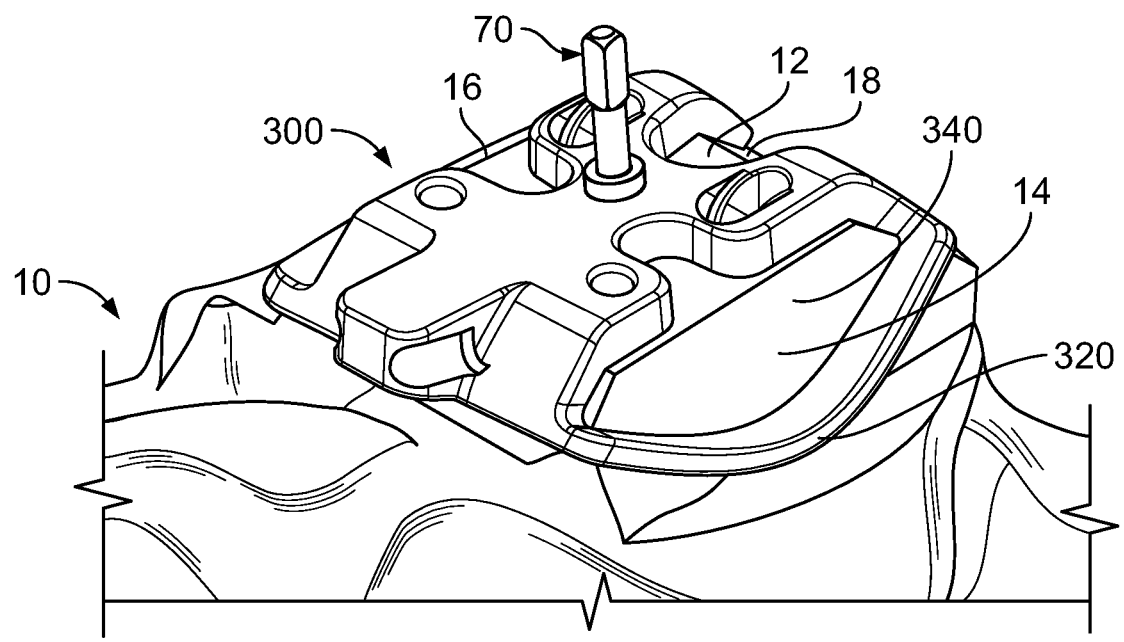
FIGS. 13-14 illustrate a surgical guide structure positioned on the talus in further steps of the method.

Returning to the apertures, those in the surgical guide structure of the depicted embodiment are of varying shape. Apertures 366 and 368 are cylindrical, as shown in the section view of FIG. 10, and extend in a direction orthogonal to top surface 310. Aperture 370 is similar to apertures 366, 368. However, among each other, apertures 366, 368, and 370 may vary in shape and size. For example, aperture 370, serving a different purpose than apertures 366, 368, may be of a different size. As noted above, apertures 362, 364 are defined by walls at varying angles relative to top surface 310 of the guide structure. In the depicted embodiment, apertures 362, 364 of generally the same shape, and thus aperture 362 shown in detail in FIGS. 10 and 11 is representative. As can be seen in the figures, toward first end 301 of the guide are walls 363C that are orthogonal to top surface 310, while on the opposite side of aperture 362, walls 363A-B taper outward from the bottom surface of guide structure 300 toward the top surface such that the aperture has a larger cross-sectional area at the top surface. More particularly, FIGS. 10 and 11 show how the taper of aperture 362 is staggered and in this manner, there is a first tapered wall 363A from the bottom surface and then a second tapered wall 363B, separated from the first by a step 369. The step is shown in FIG. 10 and the U-shape of the step is shown in FIGS. 11 and 13. In variants, the shape and size of the step may vary from that shown. Further, in other variations, tapered portions of the wall may be continuous through a depth of the guide structure without any steps. The sloping surface of walls 363A-B transitions to the right angle walls 363C on the lateral sides of aperture 362, as shown in FIG. 11. Guidance for drilling holes perpendicular to top surface 310 of guide structure 300 is provided by right angle walls 363C during the drilling procedure. To drill holes at a different angle, the tapered wall surface defines a transverse direction for a path of the aperture through the surgical guide structure. In this manner, in addition to being transverse to top surface 310, apertures 362, 364 are transverse relative to apertures 366, 368. As depicted, apertures 362, 366 are nearly symmetrical to apertures 364, 368 about axis 50.

Figure 15A:
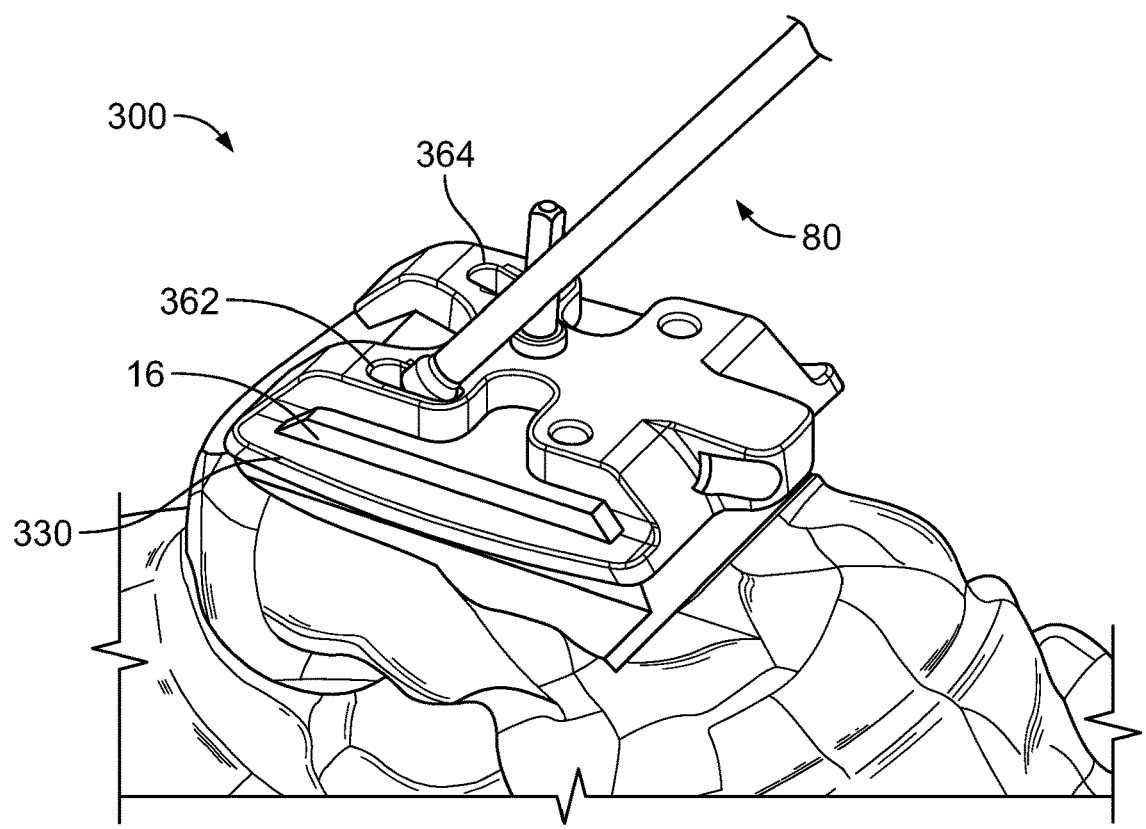
FIGS. 15A-B depict an alternate step to that shown in FIG. 14 where holes are drilled at an acute angle relative to the resected top surface of the talus.
Figure 15B:
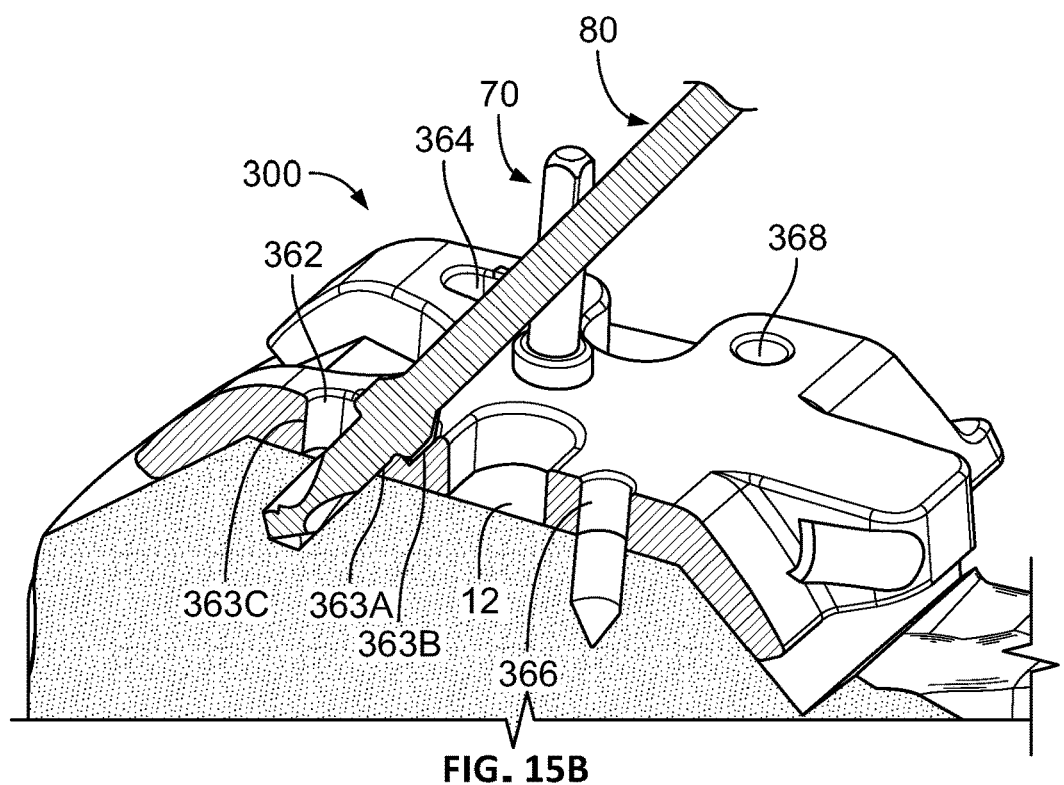

The shape and size of apertures 362, 364 accommodates placement of a drill bit therein either at a right angle or an acute angle relative to a surface of the guide structure. A slope of walls 363A-B for aperture 362 and corresponding walls for aperture 364 provides for an acute angle approach from an anterior direction. The inclusion of apertures 362, 364 as described herein increases the options available to a surgeon for accessing the guide structure when the guide structure is positioned on a talar bone to create holes in the talus. If it is not possible to drill perpendicular to the top bone surface, drilling may be at an acute angle, as shown in FIGS. 15A, 15B, and described in greater detail as part of the method embodiments herein. In variants, the shape and the size of the apertures may be varied to accommodate hole formation instruments other than drill bits. Further, any of the embodiments of the disclosure referencing apertures sized for a drill bit is contemplated as having apertures that may vary to accommodate hole formation instruments other than drill bits.

The surgical guide structure may be varied in many ways. In some examples, the surgical guide structure may be varied in ways similar to those described for the trial implant above. For example, the openings, i.e., windows, between the main body and the outer portions may also vary in shape and size to suit intended applications. The opening sizes may vary in tandem relative to the above described embodiment, or the opening on one side may vary in size and shape relative to the other opening. In other examples, the number, size, and/or location of the apertures may be varied to accommodate the type of implant intended for placement. Similarly, the apertures with tapered walls may include walls having any variation of taper along a wall depth relative to the top surface of the guide structure. A maximum angle of the taper may also vary to accommodate alternative uses. For example, the posterior apertures may have tapered walls with a maximum angle of 20 degrees relative to an axis orthogonal to the top surface of the guide structure. The tapered portion may have no step or where there is a step, its width and depth relative to the top surface of the guide structure may vary. The characteristics of the apertures may be such that each is unique and independent of the others or so that groups of apertures share physical characteristics. In other examples, the neck region near the mid point of the guide structure length may be narrower or wider than that of the above embodiment. The fork shaped extensions and central extension may also vary in size and dimension.

Additionally, the overall shape of the main body of the surgical guide structure, such as the ratio of its length to its width, may vary to suit an applicable bone geometry, for example. Similar principles apply to dimensions of the outer portions. For example, the depicted radius of the curved outer portion may vary from that shown in FIG. 7. In other examples, the shape of the surgical guide structure may also be varied for applications in joints other than the ankle. Thus, although certain embodiments above describe the surgical guide structure as shaped for use in procedures involving the ankle, the trial implant may also be shaped for seating on resected bone surfaces in other joints. In such cases, the trial implant may include windows and/or recesses so that two, three, four, five, or more resected surfaces are visible. Manufacture of the surgical guide structure may be through known procedures or, alternatively, a custom surgical guide structure may be formed through ALM fabrication processes, such as those described above for the trial implant.

Figure 23:
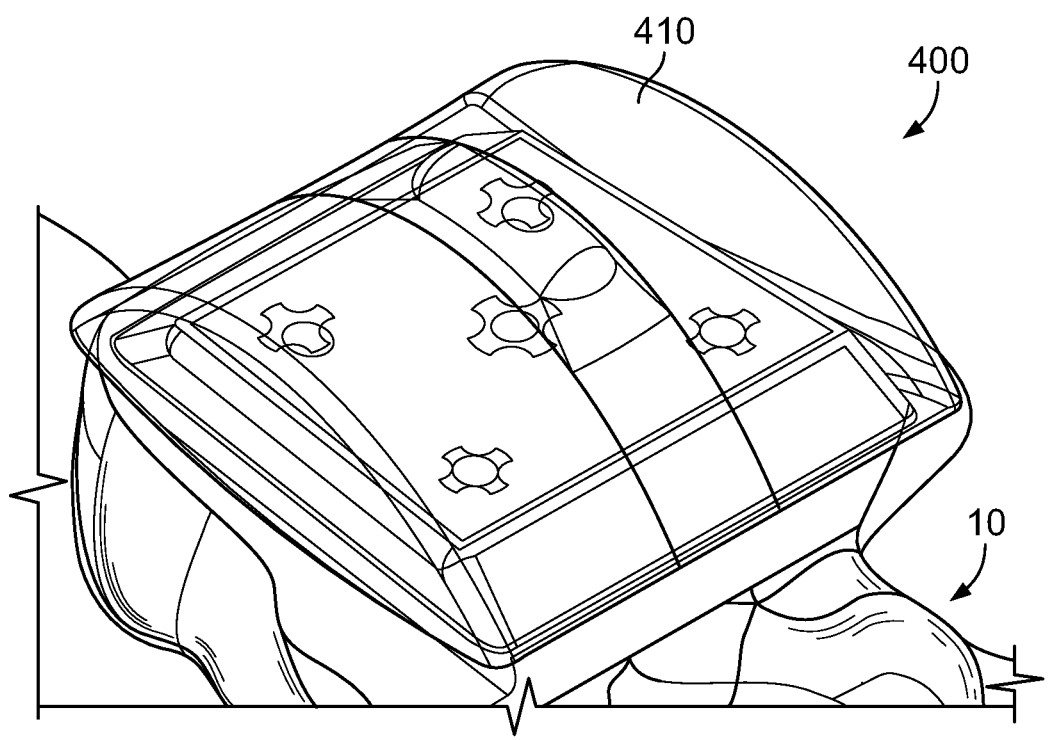
FIG. 23 illustrates a talar implant in phantom and positioned on a prepared talar surface.
Figure 24:
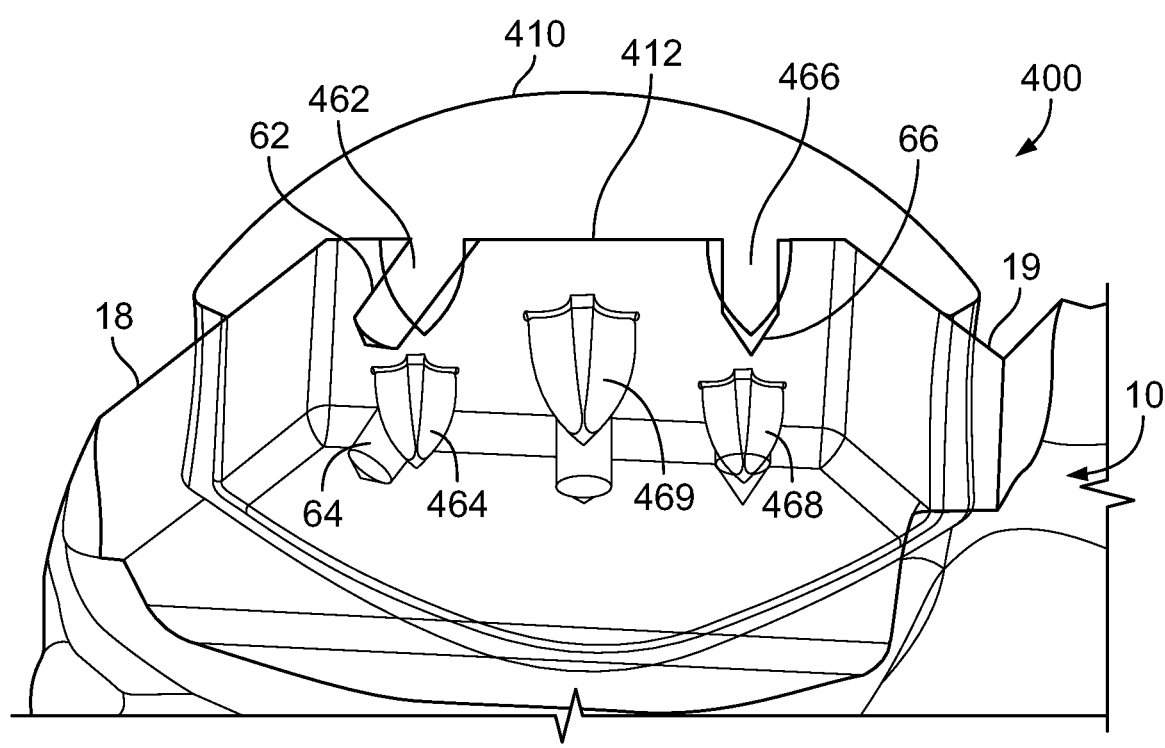
FIG. 24 illustrates a sectional view of the talar implant of FIG. 23.

In another aspect, the present disclosure relates to systems for joint replacement. In one embodiment, a system includes surgical guide structure 300 as shown in FIG. 7 and a talar implant 400, as shown in FIG. 23. In this system, surgical guide structure 300 is sized, shaped and includes apertures therethrough such that when it is positioned on resected surfaces of a talar bone, holes in the talar bone may be drilled in an accurate manner for the placement of talar implant 400. In particular, apertures 362, 364, 366, 368 and 370 (e.g., FIG. 7) are positioned on surgical guide structure 300 in a manner that corresponds to locations of protrusions 462, 464, 466, 468 and 469 of implant 400 (e.g., FIG. 24). In at least this manner, surgical guide structure 300 relates to talar implant 400. In FIG. 24, a section view of talar implant 400 reveals spike protrusions 462, 464, 466, 468, 469 that are orthogonal to a bottom surface 412 of the implant, and an orientation of such spikes relative to holes 62, 64, 66, 68, 69 in bone 10. Recall that holes 62, 64, 66, 68, 69 are the product of drilling via surgical guide structure 300. It can be seen in FIG. 24 that spikes from implant 400 may be positioned in a respective hole of bone 10 even when the hole is drilled at an acute angle. In particular, spike protrusions 462, 464 are at an angle relative to holes 62, 64. Implant 400 also includes a convex top surface 410 shaped to form an articulation surface, such as with a bearing placed between the tibial component and the talar component. The system may be varied to include any combination of devices as contemplated in this disclosure. For example, another system may include a trial implant and a permanent implant.

In another aspect, two or more of the above trial implants, implants, tools, instruments and other devices may be included together as a kit. In one embodiment, a kit is contained in a single package as a system or in multiple packages that may be selected as needed by the operator to form a system. For example, such a kit may include a trial implant, a talar implant and a surgical guide structure. If the kit includes more than one trial implant, surgical guide structure and/or talar implant, the plurality of trial implants, surgical guide structures and/or talar implants may vary in overall size, opening sizes, aperture sizes, as applicable, materials, or the like, from which the most suitable elements may be chosen for a particular surgical procedure. In other examples, the kit may include one or more of a trial implant, a talar implant and/or a surgical guide structure. Any combination of trial implants, implants, tools, instruments and other devices may also be included in a single package or in separate packaging which are later brought together as a kit.

The kit may be varied in many ways. For example, it is contemplated that any combination of the devices described herein may be included as part of a kit. This may be in the form of a kit of the above embodiments combined with one or more of a trial bearing, a ruler, a joint space evaluator, a barrel hole plate, a thread pin, a forceps and/or a drill. Such elements may be included as single elements or more than one may be included. Additionally, to the extent other tools or devices are used in conjunction with the devices described herein, such tools or devices may also be included in the kit. The various combinations of elements of any contemplated kit may be included in a single package or distributed among multiple packages. In other examples, the kits contemplated herein may be accompanied by an instruction manual on how to perform one or more of the methods of using the contents of the kit.

In another aspect, the present disclosure relates to methods of using trial implants, implants, tools, instruments, devices, systems and/or kits to perform one or more stages of surgery for joint replacement. In one embodiment, surgical guide structure 300 is used to prepare pilot holes, also referred to as holes, in a resected talar bone surface as part of an ankle replacement procedure. The talar bone is resected by any method known in the art, such as those described in U.S. Pat. Pub. No. 2012/0130376, hereby incorporated by reference herein in its entirety. The purpose of the holes is to facilitate placement of a trial implant, such as trial talar implant 100, or a permanent implant, such as talar implant 400. The method of preparing the talar bone for drilling of holes begins with placement of surgical guide structure 300 onto a talar bone surface. In the depicted embodiment, surgical guide structure 300 is placed onto talar bone 10 shown in FIG. 12. Talar bone 10 is prepared through resection of several surfaces as depicted in FIGS. 12 and 17 including top surface 12, anterior surface 19, posterior surface 18, lateral surface 14 and medial surface 16. Although the foot is depicted in FIG. 12 as having a particular orientation relative to tibia 20, such orientation is merely exemplary and performance of the methods as described herein do not require the particular orientation of the foot relative to the tibia as illustrated.

Figure 14:
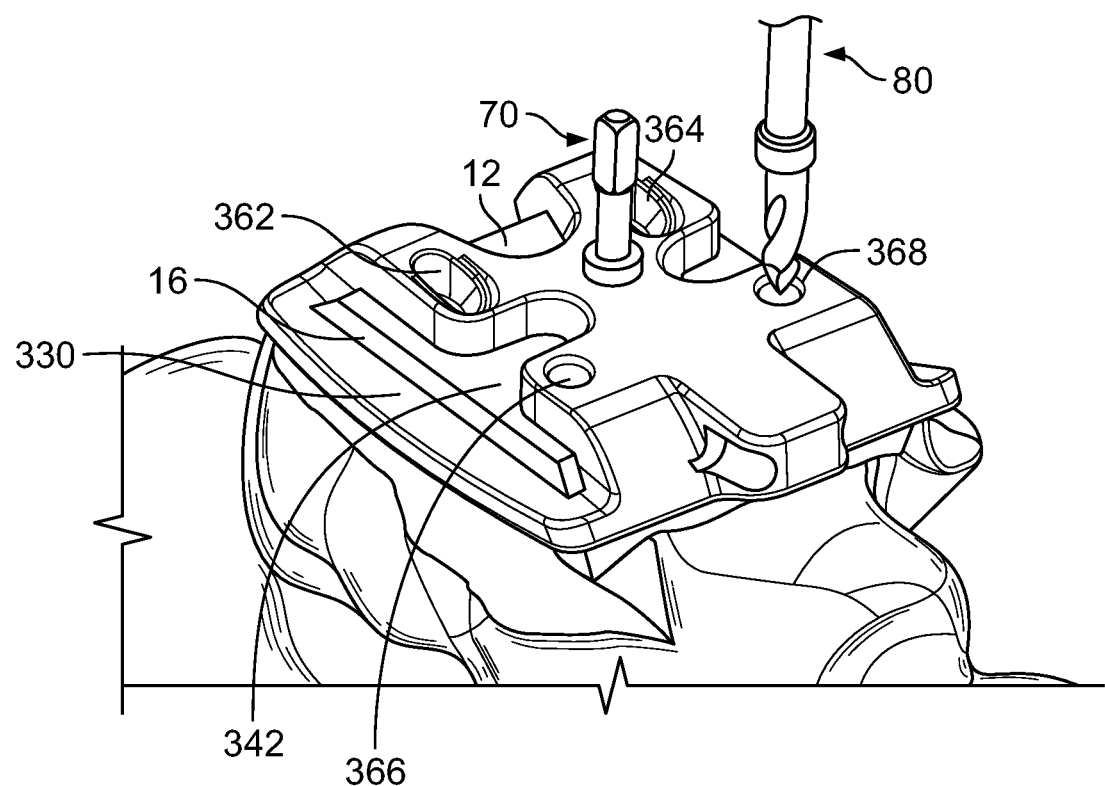

Using a tool such as forceps, surgical guide structure 300 is held and transported into position on talar bone 10, fitting onto the resected surfaces as described above and as shown in FIG. 13. In particular, bottom surface 350 (FIG. 8) corresponds to top resected surface 12, surface 352 corresponds to anterior resected surface 19, and surfaces 354A-B correspond to posterior resected surface 18. The location of the resected surfaces relative to the surgical guide structure positioned on the bone is evident with a view to FIG. 13. The resected surfaces are shown in isolation in FIG. 17. Surgical guide structure is shaped and includes openings so that multiple resected surfaces remain visible when surgical guide structure is positioned on the talus. As shown in FIG. 13, for example, opening 340 of surgical guide structure 300 permits the viewing of both top and lateral resected surfaces, 12 and 14 respectively, while opening 342 permits the viewing of both top and medial resected surfaces 12 and 16, respectively, as best shown in FIG. 14. By viewing resected surfaces 12, 14, 16, 18 of talus through openings 340, 342 and in between forked sections 312, 314, alignment of the seating of surgical guide structure 300 for drilling of holes in surface 12 may be verified and adjustments made as needed.

Continuing with this embodiment, to hold surgical guide structure 300 in place, a pin 70 is inserted through central aperture 370 of the surgical guide structure, as shown in FIG. 13. The pin 70 may be threaded and is inserted into aperture 370 by hand without tools so that pin 70 is not over inserted. In a variant, a tool may be used to insert pin 70, although in such cases, a final stage of advancement will be performed manually to ensure that pin 70 is not over inserted. By placing pin 70 through surgical guide structure 300 and into talus 10, an added level of securement to the bone is provided in addition to that provided by outer portions 320, 330 and tapered bottom surfaces 352, 354A-B. This ensures that the guide structure does not move relative to the talus while drilling additional holes in talus 10 or while viewing the resected bone surfaces.

With guide structure 300 secured to talus 10, holes are drilled in preparation for trial and implant placement. To create the holes, a drill 80 is used, the drill shown being inserted into aperture 368 in FIG. 14. Holes are created by drilling through each of apertures 362, 364, 366 and 368. Relative to the anatomy of the patient, apertures 362, 364 are posterior and apertures 366, 368 are anterior. Each hole is made at a ninety degree angle relative to top surface 12 of talus 10. When complete, drill 80 will have created four holes, as shown with guide structure 300 removed in FIG. 17. Alternatively, when it is not possible to create holes perpendicular to top surface 12 on the posterior side (i.e., through apertures 362, 364), for example, due to operational space constraints, holes may be created at an angle. One example of this variant is shown in FIGS. 15A-B, which illustrates the creation of a hole at an angle through aperture 362. Drill 80 is inserted on an anterior side of aperture 362 in a manner so that it is aligned with walls 363A-B. In this manner, walls 363A-B function as a guide for drill 80. As depicted, drill 80 is advanced until a shoulder on drill 80 is obstructed by the step between walls 363A and 363B, as best shown in FIG. 15B. The hole created through such drilling may be at any angle relative to an axis perpendicular to the top surface of the guide structure, for example, up to 35 degrees. In this manner, the drill bit trajectory may be at 10 degrees, 20 degrees, and so on.

Figure 16:
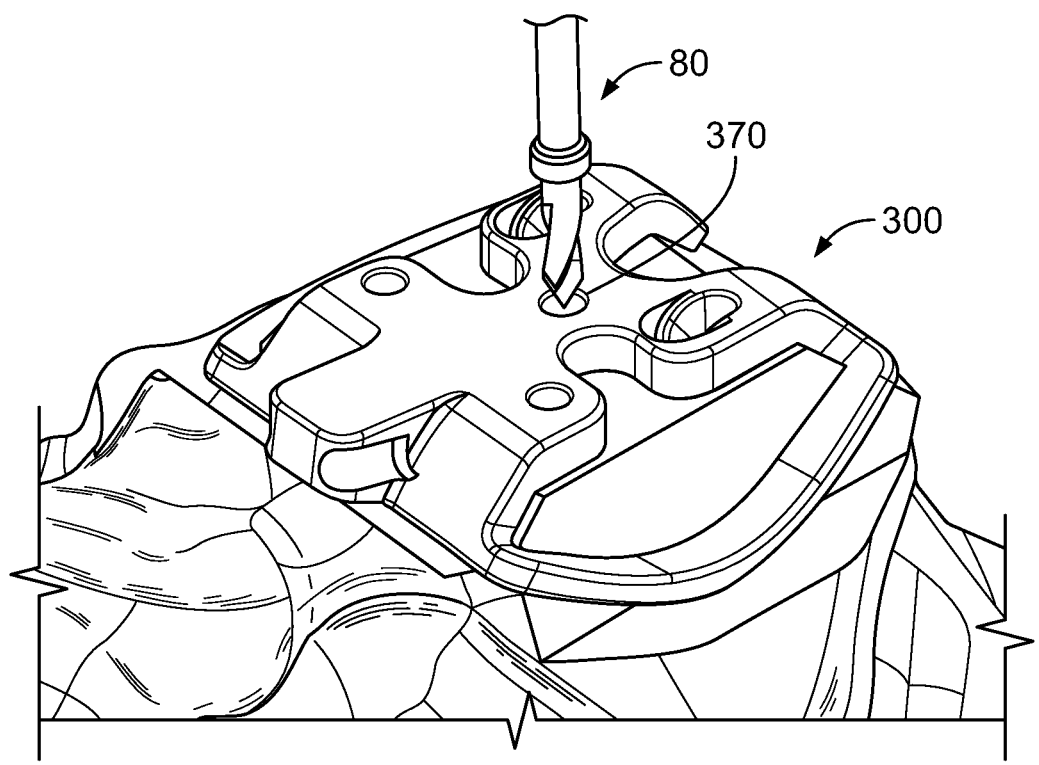
FIGS. 16-17 depict removal of the surgical guide structure according to further steps of the method.

Once all pilot holes are created in the talus, the pin is removed from within aperture 370 of guide structure 300. (FIG. 16 depicts the guide structure with the pin removed). To ensure guide structure 300 is not removed with threaded pin 70, guide structure 300 may be held down on the bone while threaded pin 70 is removed. With aperture 370 clear of obstructions upon the removal of pin 70, drill 80 is used to drill a fifth hole 69 in talus 10 central to the other four 62, 64, 66, 68. The appearance of talus 10 following creation of all five holes is shown in FIG. 17. Following creation of these holes, an implant can be seated onto the prepared talar bone, or alternatively, a trial implant may be seated on the prepared bone to ensure that a permanent implant will seat properly and be properly aligned with the tibial bone and/or another implant component.

Figure 20:
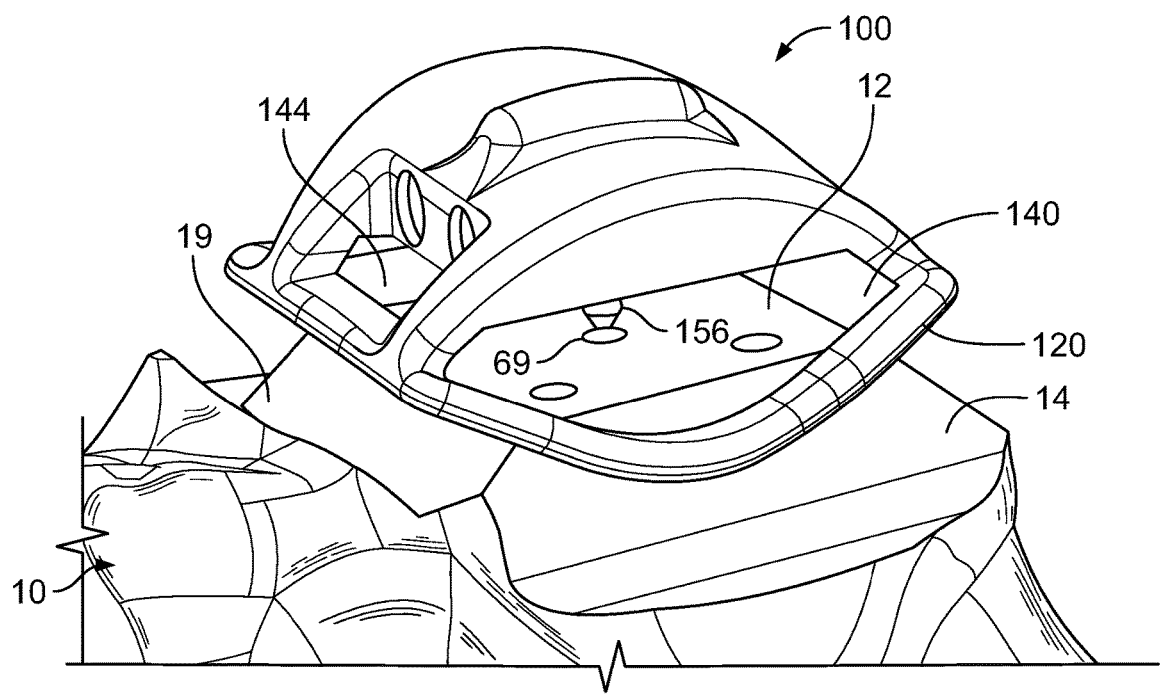
FIGS. 20-22 depict placement of a trial implant on the prepared talar surface according to further steps of the method.

In one embodiment, a trial implant is used to ensure a permanent implant will seat correctly on top of the talus and to verify that a range of motion for the permanent implant, e.g., implant 400, will be sufficient relative to the tibia and/or another implant component. In this embodiment, talar bone 10 includes several resected surfaces so that it is ready for placement of trial implant 100 thereon. For purposes of illustration, talar bone 10 may include resected surfaces 12, 14, 16, 18 and 19 as shown in FIG. 17. Each resected surface abuts at least one other resected surface in the illustrated preparation. For example, top surface 12 abuts anterior surface 19. Initially, a tool, such as a forceps (not shown) is used to place trial implant 100 on the talar bone. To align trial implant 100, protrusion 156 is positioned over hole 69, as best shown in FIG. 20. FIGS. 21 and 22 illustrate how trial implant 100 appears when completely advanced onto talar bone 10. If trial implant 100 is properly seated on the talus, top resected surface 12 will be flush with lower surface 150 of trial implant 100. To verify that the trial implant is fully seated on the talus, windows 140, 142, 144 allow for viewing of the talar surface while the trial implant is in place on talus 10. Seating of trial implant 100 on lateral resected surface 14 is viewed from opening 140, as shown in FIG. 21. Seating on anterior resected surface 19 is viewed through opening 144 as also shown in FIG. 21. Seating on medial resected surface 16 is viewed through opening 142, as shown in FIG. 22. Through the various openings, adequacy of the seating of the implant may be verified. As shown in FIG. 21, several resected surfaces are visible when trial implant 100 is seated on bone 10. These include top surface 12, medial surface 14, and anterior and posterior surfaces 19 and 18. This is made possible in part by lateral branches 124, 126 of the outer portions extending from the main body, which provides space between the top resected surface and the side surface 118.

Figure 19:
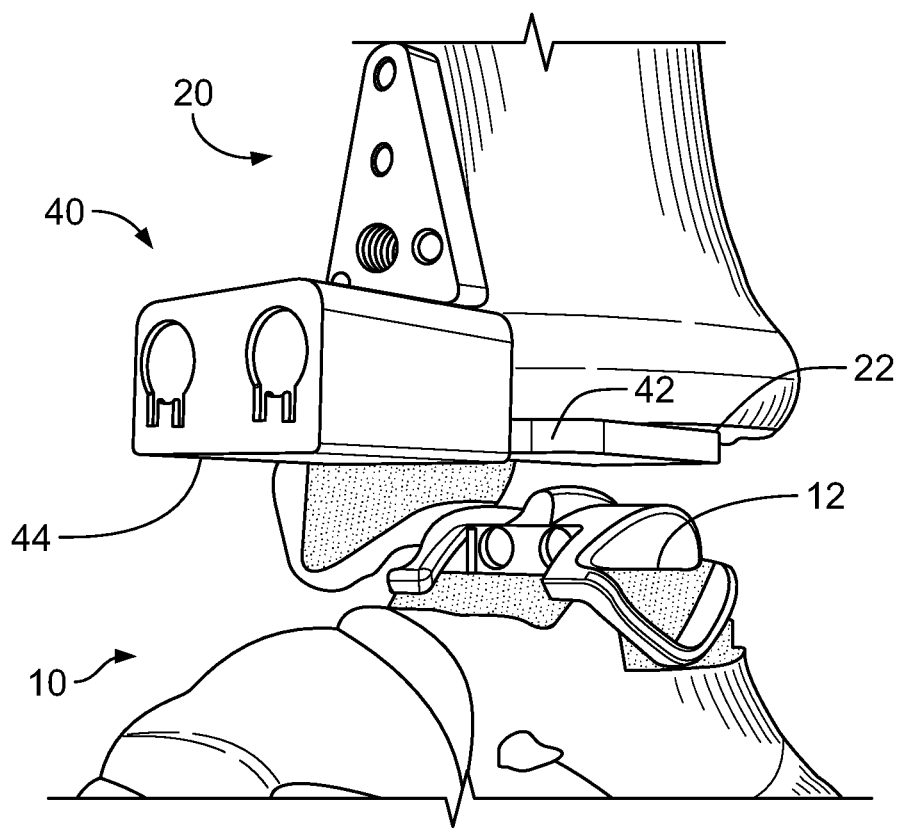
FIG. 19 depicts placement of a barrel hole plate onto the tibia according to a further step of the method.

In another embodiment, the method also includes verification of the range of motion for the final implant using the trial implant. Prior to performing such verification, a barrel hole plate (e.g., barrel hole plate 40 in FIG. 19) is first positioned on a resected distal surface of tibia 20, as shown in FIG. 19. In some alternatives, additional procedures may be performed to prepare the tibia prior to placement of the barrel hole plate, such as verification of the tibial implant size and using the barrel hole plate to drill holes in the tibia in preparation for tibial implant placement. A trial bearing (not shown) is inserted in between trial implant 100 and barrel hole plate 40 in the ankle joint space. If a gap of more than 1 mm exists between the trial bearing and the adjacent components, the trial bearing is replaced with a trial bearing of a larger size. Once a trial bearing of an appropriate size is in place, ankle stability is assessed by rotating the foot of the patient about the ankle. At the time of assessing ankle stability, the size of the trial bearing may also be reassessed. Once tibial and talar implants are in place with a chosen trial bearing, the spacing between each is evaluated to determine whether there is a gap on only one side of the trial bearing between the bearing and one of the tibial and talar implants. If so, ligament release may be performed to balance the ankle joint. Following ligament release, a larger trial bearing is used to reassess whether the proper bearing size has been identified.

In a further embodiment, a surgical method includes using surgical guide structure 300 as described above (see FIGS. 12-17) to prepare holes in a resected talar bone surface for the placement of a trial implant or a talar implant in a talar bone. The method also includes placing trial implant 100 onto the prepared talar surface to make sure the implant will seat correctly on top of the talus and to verify that a range of motion for the final implant will be suitable, as described above (see FIGS. 20-22).

Figure 18:
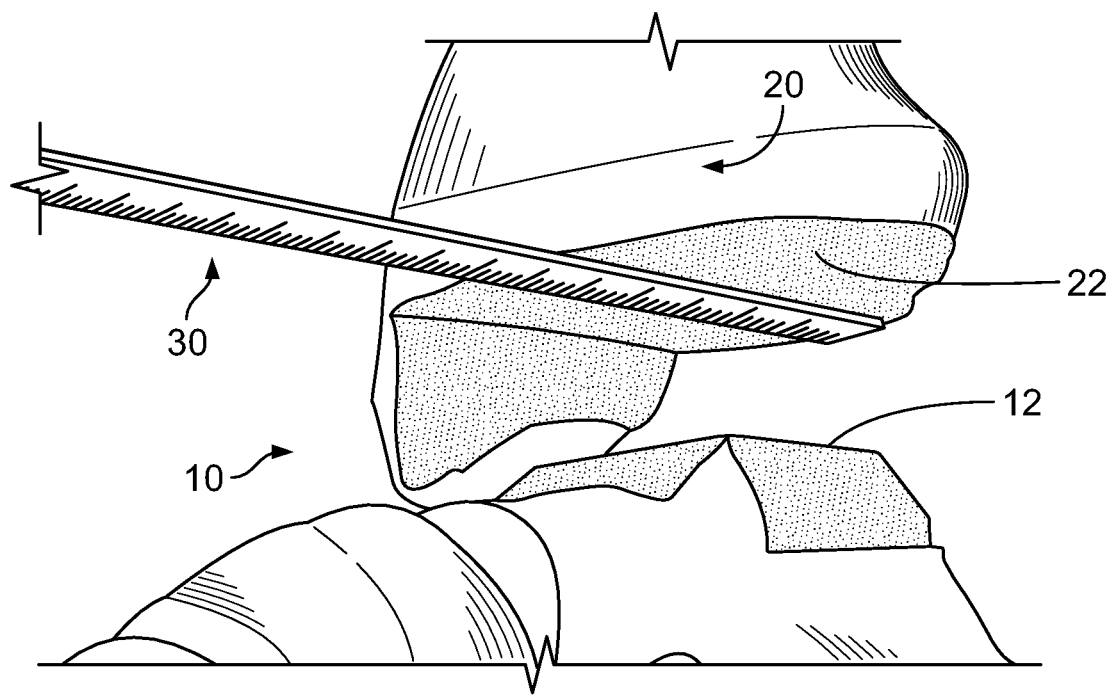
FIG. 18 depicts a step of evaluating the dimensions of a prepared tibia for determining the proper size of a tibial component according to a further step of the method.

In a variant, the method includes additional steps between using surgical guide structure 300 to create holes in the resected talar bone surface and placement of trial implant 100. Once holes in the talar bone are drilled as described above, the talar bone appears as shown in FIG. 17. At this time, a size of a tibial implant component is determined. A ruler 30 is placed underneath a previously resected underside surface 22 of tibia 20, as shown in FIG. 18. To obtain the relevant dimension, ruler 30 is advanced to the posterior edge of the resected surface. Then, an anterior/posterior dimension of the tibia is obtained. As needed, this dimension may be measured at one or more locations between the medial and lateral sides of the tibia. A tibial component is then selected that corresponds to the measured dimension. With the measurements complete, an appropriate barrel hole plate 40 is selected and then inserted over resected surface 22 of tibia 20, as shown in FIG. 19. With the barrel hole plate in place, space in between the plate and the resected talar surface is evaluated to determine whether it is adequate for the implants to be used in the ankle replacement. Etching 44 on a bottom surface of barrel hole plate 40 mimics a physical location of a bottom surface of the tibial implant to assist with the determination. In some variants, the method may be complemented with fluoroscopy to provide additional information regarding positioning of the barrel hole plate. Once the above steps are complete, trial implant 100 is placed on top surface 12 of talus 10, as described above, and as shown in FIGS. 20-22.

In another embodiment, a surgical method includes placing trial implant 100 onto a prepared talar surface to make sure the implant will seat correctly on top of the talus and to verify that a range of motion for the final implant will be suitable, as described above (see FIGS. 20-22). Upon completing the necessary measurements and removing the trial implant, a talar implant 400 is retrieved. A tool, such as a forceps (not shown), is used to grasp talar implant 400 and place it onto talus 10. In a variant, talar implant 400 may first be attached to a talar implant holder, and the forceps may grasp the talar implant holder and then guide the talar implant into place on the talus. Where the implant includes a central protrusion, such as protrusion 469 of talar implant 400 shown in FIGS. 23 and 24, such protrusion 469 is aligned and otherwise positioned over hole 69 and then advanced into hole 69, hole 69 being through top resected surface 12 of talus 10. Similarly, protrusions 462, 464, 466, 468 are aligned with respective holes 62, 64, 66, 68 in the talus to position and secure talar implant to the talus, as shown in FIG. 24. When one or more of holes 62, 64 have been drilled at an angle, protrusions 462, 464 enter holes 62, 64 and at least a portion of such protrusions enter the bone adjacent to the bone hole. In this manner, a portion of protrusions 462, 464 is in the hole while another portion is in the bone. To fully secure and seat talar implant 400 into place, a mallet or other tool may be used to apply an impaction force onto the implant. When fully seated, surface 412 of talar implant 400 is flush with top resected surface 12, as shown in FIG. 24. Optionally, a joint space evaluator (not shown) may be inserted into the ankle joint space to verify that the talar implant is fully seated. Similarly, fluoroscopy may be used to confirm that the talar implant is properly seated in one or more of the anterior/posterior directions and medial/lateral directions.

In a variant, the immediately preceding embodiment also includes additional preparation after evaluation of the talar resections with the trial implant and drilling of holes in the talus (as shown in FIGS. 20-22). These include preparation of the tibia for implant placement. A poly trial or a tibial barrel hole wedge may be used to verify that a prepared, e.g., resected, tibial surface facing the ankle joint is finished to be flush with a barrel hole plate to be placed thereon. Such verification allows for improved positioning of the barrel hole plate on the prepared tibial surface adjacent the trial implant. When the resected tibial surface is deemed ready, the barrel hole plate is secured to the tibia with fixation pins. Holes are then drilled in the tibia, one at a time, through openings in the barrel hole plate to allow for insertion of the tibial implant.

Other steps may include assessment of a size of the bearing for the joint. To perform this assessment, a trial bearing is placed into the joint space between the trial implant and a plate of the barrel hole plate. The ankle is then rotated to evaluate the implant sizes and also to assess ankle stability. If a gap of more than 1 mm is observed between the bearing and the adjacent components, the trial bearing should be substituted with a bearing one size larger and the same assessment should be performed again. Any variation in a gap between the bearing and the adjacent barrel hole plate or trial implant from one side to the other in a lateral direction suggests that ligament balancing may be necessary. Once a size of the bearing is confirmed, the trial and the barrel hole plate are removed. Once the site is cleared as needed, talar implant 400 is placed into position on the talus, as described above.

In yet another embodiment, a surgical method includes using surgical guide structure 300 as described above (see FIGS. 12-17) to prepare holes in a resected talar bone surface for the placement of a trial implant and a talar implant therein. It also includes placing trial implant 100 onto the prepared talar surface to ensure the implant will seat correctly on top of the talus and to verify that a range of motion for the final implant will be suitable, as described above (see FIGS. 20-22). Finally, the method concludes with the placement of a talar implant, as described above, where the seated implant is as shown in section in FIG. 24. This method may be varied in many ways. For example, the method may also include any number of additional steps as described in the various aforementioned embodiments.

In other embodiments, a method of placing prostheses in the ankle is performed that includes preparation of anatomy around and within an ankle joint followed by placement of a talar implant. In this method, a tibial alignment guide (not shown) is set up and otherwise positioned on the tibia. A pin block (not shown) is then locked into position on the alignment guide with adjustments made as necessary. Further alignment of the tibial alignment guide may also be performed prior to tightening to fix the tibial alignment guide in place. The guide is then aligned with the coronal and sagittal plane through further adjustment of the tibial alignment guide and through attachment of a parallel alignment guide (not shown) to the tibial alignment guide. Once alignment is complete, the parallel alignment guide is removed.

With all necessary guides properly aligned, preparations are made to cut the tibia. A tibial cut guide (not shown) is attached to the pin block. To limit the amount of bone that can be resected, adjustments are made using the pin block. Fluoroscopy may be performed at this juncture to check the alignment of the cut guide and other instrumentation. Further adjustments may then be made, as needed. Pins are used to lock the amount of tibial resection and the instrumentation is ready for use. An oscillating saw is advanced into a slot of the cut guide to make a transverse distal tibial cut within the tibial cut guide while a reciprocating saw is used to make a cut along the inner edge of the medial malleolus. The tibial cut guide is then removed and the resected bone is removed.

Once the tibial resection is complete, the talar bone is prepared for resection. A talar cut guide (not shown) is placed on the tibial alignment guide and pins are inserted into the guide as needed. An oscillating saw is used to make an initial transverse distal talar cut. Then, a joint space between the talus and tibia is evaluated. Next, a template is used to determine a necessary size of the talar implant. A drill guide is attached to the template and a pin is inserted through the drill guide. With the pin in place over the talus, the pin is used to guide a datum into position on the talus. Once the datum is secured, a talar anterior/posterior cut guide is secured to the datum. This allows various tools to be used with the cut guide to make an anterior and posterior talar cut. The anterior/posterior cut guide is then removed and a talar medial/lateral cut guide is attached to the datum. Medial and lateral cuts are then made, and the medial/lateral cut guide is removed. Upon completion, the talus will have at least top, posterior, medial and lateral resected surfaces. One example of the performance of these steps is provided in U.S. Pat. Pub. No. 2012/0130376.

When surfaces of the talus are prepared, surgical guide structure 300 is used to create holes in the top resected surface of talus 10. This is followed by evaluation of sizing and positioning for the talar implant using trial implant 100. When ready, talar implant 400 is placed on talus 10. Each of the aforementioned steps may be performed as described above. To complete the surgery, steps as known to those of skill in the art are taken to implant the tibial implant. This represents the end of the procedure and is followed by closure of the incision in the patient.

The methods described above may be varied in many ways. For instance, combinations of any number of the steps in any one of the aforementioned embodiments may be performed as desired. In other examples, the methods may be performed using any structure contemplated in this disclosure. In still further examples, transport and placement of instruments, devices and implants may be done by hand without tools.

Joint Space Evaluator and Post Talar Cut Template

Figure 25:
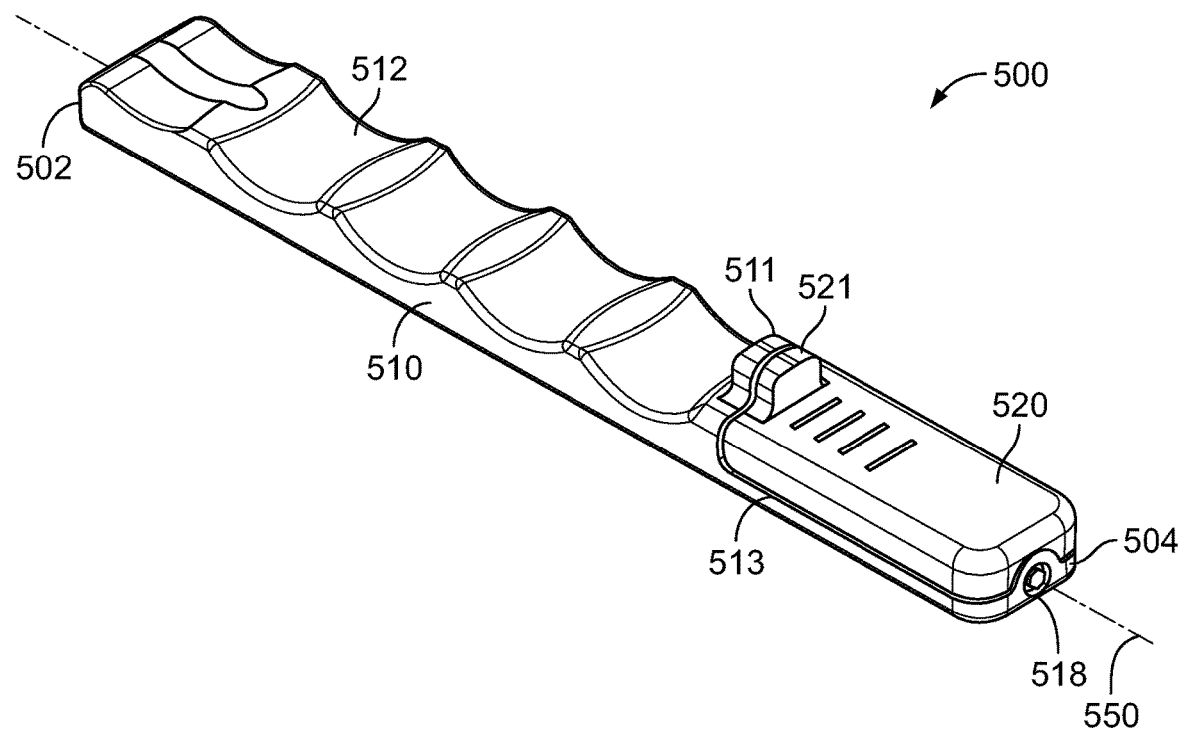
FIG. 25 is a perspective view of a joint space evaluator according to one embodiment of the present disclosure.

In one aspect, the present disclosure relates to a joint space evaluator. In one embodiment, a joint space evaluator 500 is as shown in FIG. 25. Joint space evaluator 500 includes a main body 510 and a pivoting member 520 and has a length that extends from a first end 502 to a second end 504.

Figure 26:
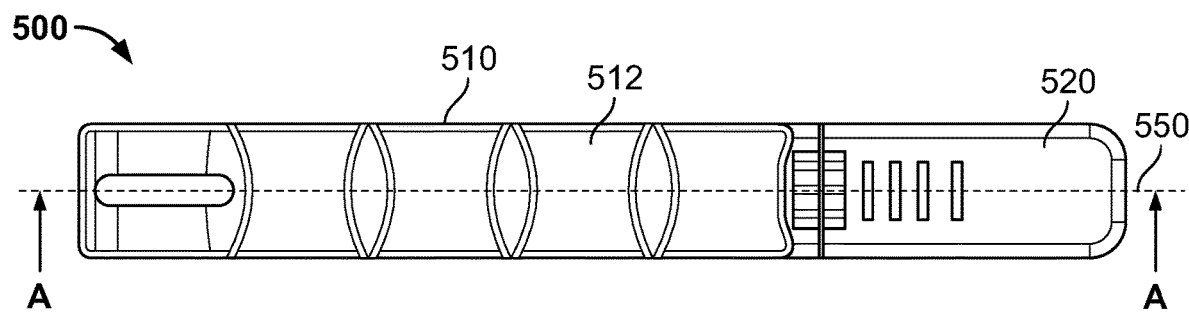
FIGS. 26-28 are various views of the joint space evaluator of FIG. 25.
Figure 27:
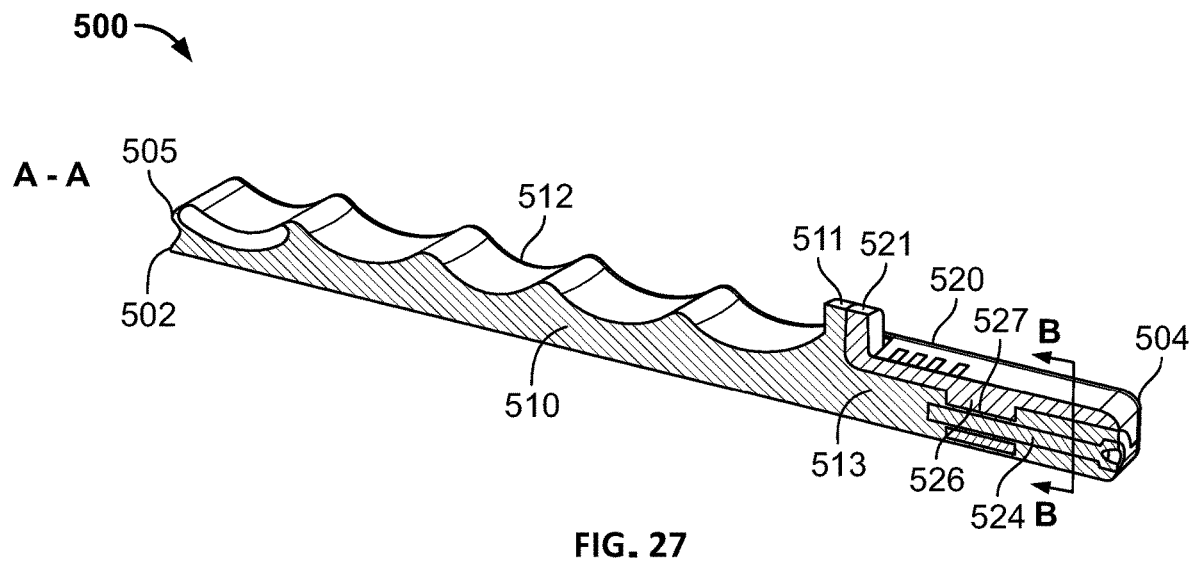
Figure 28:
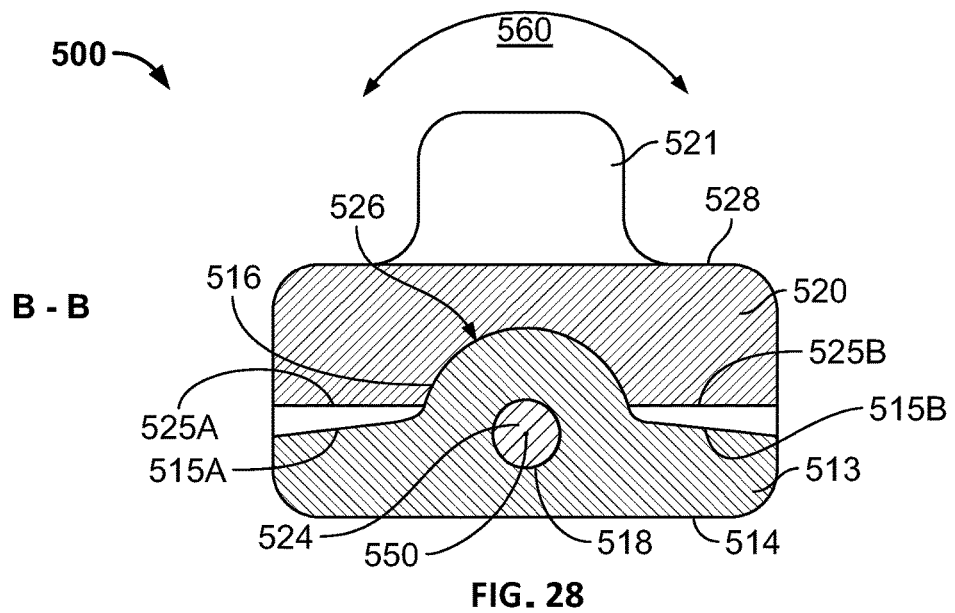

Main body 510 of joint space evaluator 500 has a linear shape (FIG. 26) and includes a series of finger grips 512 toward first end 502 and a recessed portion 513 toward second end 104. Recessed portion 513 is shaped to accommodate placement of pivoting member 520 thereon, as shown in FIG. 25, for example. In particular, recessed portion 513 includes sloped side surfaces 515A-B separated by a convex surface 516, shown in section in FIG. 28. These surfaces extend over two separate lengthwise sections of recessed portion 513, divided by an internal extension 526 of pivoting member 520, as shown in FIG. 27. As will be described further below, recessed portion 513 also includes an opening 518 extending therethrough and internal to main body 510 (FIGS. 25, 28). Opening 518 is oriented and positioned lengthwise to be aligned with a pivot axis 550 extending along the length of joint space evaluator 500, as shown in FIGS. 25 and 28. On a surface of main body 510 opposite finger grips 512 and recessed portion 513 is a flat planar bottom surface 514. (FIG. 28). At a juncture between finger grips 512 and recessed portion 513 is a fixed indicator 511. Fixed indicator 511 is in the form of a protrusion extending outwardly from the surface of main body 510 and extends further from the surface than any other part of main body 510, as best shown in FIG. 27. This aids in promoting the visibility of fixed indicator 511 from various angles.

Pivoting member 520 is shaped to nest within and engage to recessed portion 513 of main body 510, as shown in FIG. 25. Specifically, pivoting member 520 includes internal extension 526 sized to fit within a space in a central area of recessed portion 513, as shown in FIG. 27. Internal extension 526 includes an opening 527 therethrough positioned to axially align with opening 518 of recessed portion 513 when internal extension 526 is disposed in recessed portion 513. A pin 524 is disposed in the respective openings 518, 527 as best shown in FIG. 27 so that pivoting member 520 is attached to main body 510.

When attached to main body 510, side surfaces 525A-B and concave surface 526 of pivoting member 520 face sloped side surfaces 515A-B and convex surface 516 of recessed portion 513, respectively, as best shown in FIG. 28. Concave surface 526 interacts with convex surface 516 so that pivoting member 520 is pivotable relative to recessed portion 513, i.e., main body 510, as indicated by arrows 560. Because sloped side surfaces 515A-B slope downward toward outer edges of joint space evaluator 500, a gap exists between one or both of opposing surface pairs 515A-525A and 515B-525B. This provides room for pivoting member 520 to pivot relative to a position aligned with main body 510. In one example, pivoting member 520 is rotatable up to five degrees relative to main body 510 in either direction (i.e., clockwise and counter-clockwise) such that a top surface 528 of pivoting member 520 can be positioned at an angle up to five degrees relative to bottom surface 514 in either direction. Thus, the gap, i.e., the amount of room, between opposing surface pairs 515A-525A and 515B-525B is sufficient to accommodate this range of rotation. Continuing with this example, if the angle between bone surfaces is greater than five degrees during a particular assessment, the spacer will still function to indicate that tissue balancing is required as contact with opposing bones could still be possible (e.g., one of the opposing surface pairs 515A-525A and 515B-525B would be in contact, indicating to the operator that soft tissue balancing in the joint, further revision of one or more bones, or a combination of the two, may be needed). In another example, the joint space evaluator may have a shape and size tailored to a particular joint, such that the gap may be larger or smaller than this example to allow more or less relative rotation in the evaluator. In yet another example, the gap between pivoting member 520 and main body 510 may be any amount that is sufficient to provide a visual indication to a user that the joint space is uneven.

Pivoting member 520 and internal extension 526 are structured to pivot, or rotate, about pin 524 (pivot axis 550 passes through pin 524) while main body 510 remains stationary. Pivoting member 520 also includes a movable indicator 521 positioned to abut or lie adjacent to fixed indicator 511 when pivoting member 520 is attached to main body 510. When pivoting member 520 is in alignment with main body 510, as shown in FIGS. 25-28, movable indicator 521 is aligned with fixed indicator 511. However, when pivoting member 520 is not in alignment with main body 510, movable indicator 521 appears offset relative to fixed indicator 511, providing a visual cue to the user that pivoting member 520 is rotated relative to main body 510. In such circumstances, top surface 528 of pivoting member 520 is not parallel with bottom surface 514 of main body 510. In one alternative, the joint space evaluator includes a movable indicator on the pivoting member with markings so that each marking, when aligned with the fixed indicator on the main body, represents an angle of a top surface of pivoting member relative to a bottom surface of the main body. The size, materials, and/or shape of the joint space evaluator in this alternative may be different to accommodate markings or other indicia. For example, the fixed indicator 511 may be larger relative to the movable indicator 521 than those shown in the depicted embodiment, such that the larger fixed indicator 511 can accommodate the markings. In another alternative, the fixed indicator is transparent so that indicators on a face of the movable indicator facing the fixed indicator are visible through the fixed indicator and may line up with a centerline of the fixed indicator. In yet another alternative, the joint space evaluator includes a single movable indicator in the form of a liquid with bubble in a tube, similar to that used for carpentry.

The joint space evaluator may be varied in many ways. In one example, the recessed portion of the main body has a concave rotational surface and the pivoting member has a corresponding convex surface. Other interfacing shapes are also contemplated provided that central facing surfaces of the recessed portion and the pivoting member facilitate rotation of the pivoting member relative to the recessed portion about the pivot axis. In other examples, the indicators may have a shape other than that shown in the figures. The joint space evaluator may also be modified so that the indicators are spaced apart from one another, provided that the indicators are aligned with each other when the pivoting member is level with the main body. In yet another example, the overall cross-section of the joint space evaluator may vary in shape to suit an expected space between resected surfaces or for other reasons associated with an applicable surgery. In any event, at least a portion of the top surface of the pivoting member and the bottom surface of the recessed portion of the main body that is placed between bone surfaces is planar. Similarly, an overall size of the joint space evaluator may vary to accommodate varying patient sizes. Further, elements other than a pin that allow for rotation of one member relative to another may also be positioned in the joint space evaluator to connect the pivoting member with the main body, such as, for example, a groove and pin arrangement or the like. Further, the pivoting member may be biased in a certain direction which may provide ease of use in certain techniques.

Figure 29:
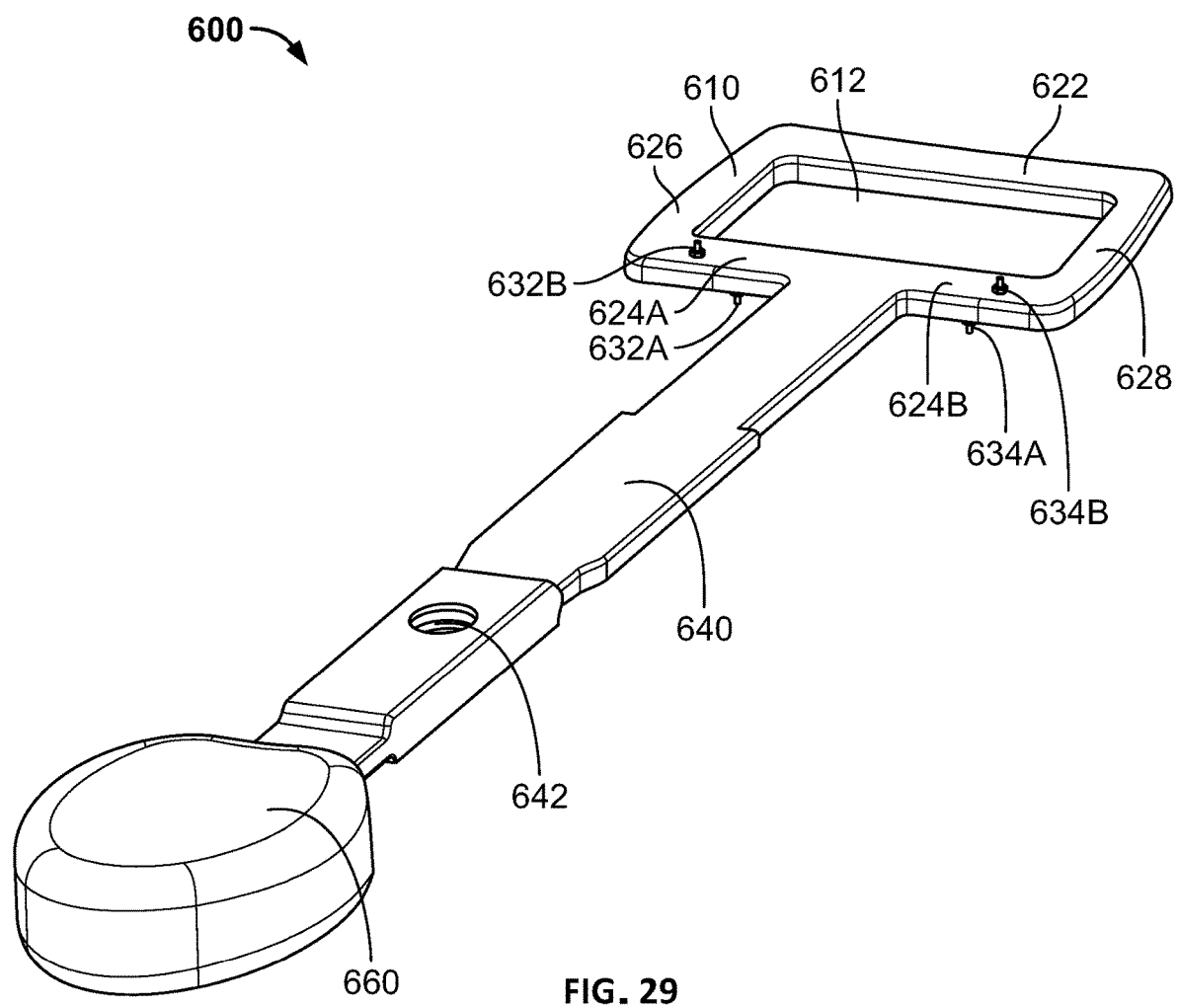
FIG. 29 is a perspective view of a post talar cut template according to one embodiment of the present disclosure.

In another aspect, the present disclosure relates to a post talar cut template, one embodiment of which is shown in FIG. 29. Post talar cut template 600 includes a template frame 610, a shaft 640 extending from frame 610, and a handle 660, the handle extending from an end of the shaft opposite the template frame.

Template frame 610 forms an enclosed perimeter with a template window 612, or opening, therein, as shown in FIG. 29. Specifically, template frame 610 has first and second inner segments 624A, 624B extending from shaft 640, each of the segments extending in opposite directions from shaft 640. Disposed on first inner segment 624A are pins 632A-B and disposed on second inner segment 624B are pins 634A-B. Pins 632A, 634A extend in a perpendicular direction away from a bottom surface of template frame 610 while pins 632B, 634B extend from a top surface of template frame 610. Pins 632A, 634A are offset relative to pins 632B, 634B. Alternatively, pins on both sides may be in line with each other. In some examples, the pins extend only from the bottom surface of the template frame. The pins engage with the talar bone to prevent slippage of the template from the talar surface while frame 610 is disposed thereon. When the pins are included on both the top and the bottom surface, such as in the embodiment depicted in FIG. 29, inclusion of the pins on both the top surface and the bottom surface provides a user with a choice of one side or the other for placement of the template onto a resected bone surface. When the pins on one side are offset relative to the pins on the opposite side, a user may have additional placement choices. Choices may be based on whether the template is used on the left or right talar bone, the overall size of the resected bone surface, or on other factors related to a particular surgery. For example, one embodiment of a template frame may be designed to be reversible such that it can be used, on one side, for one of the right or left talar bones, and on the other side, for the other talar bone. The pins may be inline or offset, as discussed above.

Continuing with the template frame 610 of FIG. 29, from ends of the inner segments extend first and second lateral segments 626, 628, each of which extend in a direction away from handle 660. In one example, first and second lateral segments 626, 628 extend away from the handle in parallel. In another example, first and second lateral segments are non-parallel. At an end of first and second lateral segments 626, 628 opposite the inner segments each lateral segment 626, 628 is interconnected by outer segment 622. In this manner, an inner edge of each of inner, outer and lateral segments 622, 624A-B, 626, and 628 define an outer dimension of window 612. As seen in FIG. 31, template window 612 is a four sided polygon with lateral segment 628 having an inner edge tapering toward a central axis 1050 of shaft 640 in a direction away from shaft 640.

In the depicted embodiment, an area within an outer perimeter of the template is less than two times the size of an area of template window 612. Similarly, a first distance between outer edges of lateral segments 626 and 628 is less than two times a second distance between the inner edges of lateral segments 626 and 628. Continuing to refer to FIG. 29, a bottom surface of template frame 610 is planar. The top surface of template frame 610 is also generally planar, though in variants it may have a varying non-planar profile.

Shaft 640 is generally linear in shape and includes an engagement feature in the form of a threaded aperture 642 therethrough. Aperture 642 is oriented so that it passes through shaft 640 in a direction perpendicular to a plane through template frame 610. As depicted in FIG. 29, threaded aperture 642 is closer to handle 660 than template frame 610. Threaded aperture 642 is sized to accommodate securement of a drill guide therein, discussed in greater detail in the method below. Further, shaft 640 includes a surface shape to accommodate placement and securement of a drill guide thereon.

The post talar cut template may be varied in many ways. In certain examples, the window in the template frame may be larger or smaller relative to an overall dimension of the template frame than shown in FIGS. 29 and 31. The window may also have a shape that varies from that of the outer perimeter of the frame. Still further, the various segments forming the perimeter of the frame may create any shape desired. In some examples, the outer perimeter of the frame is shaped to match a footprint of a talar implant. For instance, FIGS. 31-32 illustrate lateral segments 626, 628 which are not parallel to one another and define an outline of a talar implant. In other examples, the lateral segments may be parallel with one another. Similarly, inner 624A-B and outer 622 segments may be transverse to one another or parallel. Further, any one segment may be transverse to another segment and may be at an acute or oblique angle to an adjacent segment. In other examples, the post talar cut template may be thicker or thinner than shown in the figures.

In still further examples, the threaded aperture may be positioned elsewhere on the shaft or may be substituted with another engagement feature to complement an engagement feature on a drill guide. In yet another example, a width of the shaft may also be greater or less than that shown in the figures relative to the template frame width. Of course, the handle may also be any desired size or shape.

One advantage of the post talar cut template is that a resected bone surface is viewable while the template is positioned on the bone, thereby allowing a user to determine whether the previously prepared bone resection (e.g., talus) facing an opposing bone (e.g., tibia) is flat and otherwise accurately prepared. Further, and as described in greater detail below, the template is also advantageous in that it may be left in place and used with a drill guide to accurately insert a datum pin into the talus, thereby preparing the talus for further resections. This function obviates the need for the removal of the template and the placement of a separate tool to perform the same task.

In another aspect, the present disclosure relates to systems for joint replacement. In one embodiment, a system includes a post talar cut template 600, a drill guide 700, and a datum pin 800, as shown in FIGS. 31-35. The drill guide is attachable to the template while the datum pin is insertable into the drill guide. In combination, these instruments are used to identify a proper implant size and to establish an alignment from which to perform resections around the talus via preparation for placement of a datum, among other purposes. In another embodiment, a system includes joint space evaluator 500 and post talar cut template 600, used together to ensure medial and lateral tissues at the joint are balanced and to ensure an appropriate implant size is chosen, among other purposes. Other combinations of these elements are also contemplated.

In another aspect, two or more of the joint space evaluator, post talar cut template and other instruments such as a drill guide and datum pin may be included together as a kit. In one embodiment, a kit is contained in a single package as a system or in multiple packages that may be selected as needed by the user to form a system. For example, such a kit may include one or more of a post talar cut template, drill guide and datum pin. If the kit includes more than one post talar cut template, joint space evaluator and/or other instrument, the plurality of post talar cut templates, joint space evaluators and/or other instruments may vary in overall size or material composition, from which the most suitable elements may be chosen for a particular surgical procedure. In other examples, the kit may include one or more of a joint space evaluator, post talar cut template and other instruments such as a drill guide and datum pin. Any combination of joint space evaluators, post talar cut templates and other instruments such as a drill guide and datum pin may also be included in a single package or in separate packages which are later brought together as a kit.

The kit may be varied in many ways. For example, it is contemplated that any combination of the instruments described herein may be included as part of a kit. This may be in the form of a kit of the above embodiments combined with one or more of a resection guide, implant trial, trial bearing, a ruler, a barrel hole plate, a thread pin, a forceps and/or a drill, among other instruments used in ankle or other joint surgery. Additionally, any number of other instruments may also be included such as those described above and in U.S. Pat. App. Pub. No. 2012/0130376, the disclosure of which is hereby incorporated by reference herein in its entirety. Such elements may be included individually or in sets. The various combinations of elements of any contemplated kit may be included in a single package or distributed among multiple packages. In other examples, the kits contemplated herein may be accompanied by an instruction manual on how to perform one or more of the methods of using the contents of the kit. In any kit formed of one or more components of the present disclosure, many of which are described above, each distinct component may be present as a single component or as more than one component. If multiples of a single component are present in the kit, each of the components may be the same as one another or may be different from one another in materials, dimensions, color, and/or the like.

Figure 30:
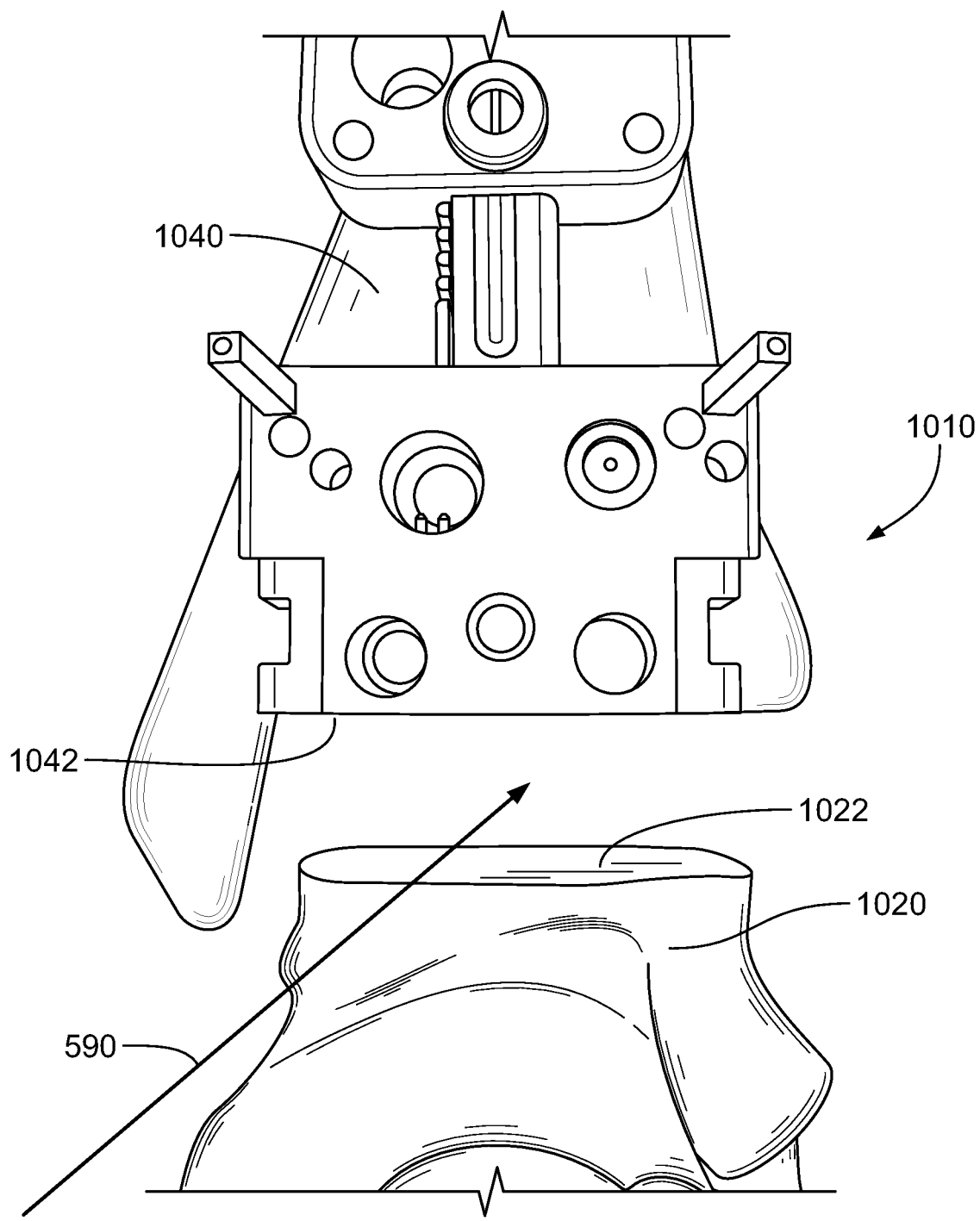
FIG. 30 is a front view of an ankle prepared for placement of the joint space evaluator according to one embodiment of a method of the present disclosure.

In another aspect, the present disclosure relates to methods of using various instruments to improve joint surgery. In one embodiment, a joint space evaluator is used, among other reasons, to verify that there is an appropriate amount of space between resected bone surfaces for the placement of implant components. The joint space evaluator also serves to verify medial and lateral soft tissue balancing. In this method, tibial and talar resections, 1042 and 1022, respectively, are prepared during ankle surgery (FIG. 30). If necessary, tools and other instruments are removed from the surgical site so that a clear path is available to access a space between tibia 1040 and talus 1020. With access clear, joint space evaluator 500 is inserted in between the resected surfaces 1022, 1042, as indicated by arrow 590 in FIG. 30. If joint space evaluator 500 does not fit, it is removed and a determination is made based on the existing conditions whether additional resection of tibia 1040 and/or talus 1020 is necessary. In many cases, additional resection will be via resection of the tibia using resection tools, as applicable. When measuring a space between the resected surfaces, existing space is verified for sufficiency with regard to placement of implant components, such as the talar implant components. In one example, 16 mm of space is necessary.

When joint space evaluator 500 is successfully placed in between the resected surfaces, indicators 511, 521 are viewed to confirm whether pivoting member 520, a proxy for the tibial resection, is in alignment with main body 510, a proxy for the talar resection. The combination of indicators 511, 521 serve as a self-leveling indicator. If each indicator 511, 521 is in alignment, such as is shown in FIG. 25, then it is confirmed that each resected surface 1022, 1042 is parallel to the other and that, as a result, no soft tissue (i.e., ligament) balancing is necessary. However, if movable indicator 521 is offset, or otherwise laterally shifted relative to fixed indicator 511 while joint space evaluator 500 is positioned between the resected surfaces, then this signals to the user that ligament balancing should be performed to level the respective surfaces. The user will determine based on the direction of the offset of movable indicator 521 whether balancing is required on the lateral or medial side of the ankle. Ligament balancing is then performed at this stage of the procedure. As ligament balancing is performed, joint space evaluator 500 self-levels so that the user can monitor the adjustment and has a clear visual cue of when balancing is complete via indicators 511, 521. Once indicators 511, 521 are aligned, joint space evaluator is removed. The use of joint space evaluator 500 in this manner is advantageous in that balancing is verified early in the ankle surgery procedure without the need for trial implants or the actual implants. Put another way, balancing is performed without the need for a range of motion test. It is also simple and surgeon friendly in that no separate task is required to monitor the leveling procedure other than ligament balancing itself.

In another embodiment, the present disclosure relates to a method of using a post talar cut template, such as post talar cut template 600, shown in FIG. 29. Initially, talar and tibial resections are prepared as part of a broader ankle procedure. A template from a series of templates is then chosen to place onto resected surface 1022 of talus 1020. The series of templates (only one shown) includes templates of various sizes to accommodate a range of talus sizes. In the embodiment depicted in FIGS. 31-35, a "LEFT XSMALL" size template is selected and used. Of course, it is contemplated that other sizes would be made available for the surgical procedure, as needed.

Post talar cut template 600 is advanced onto resected surface 1022 so that shaft 640 is aligned with a second metatarsal bone 1012 (FIG. 32). Template 600, when in place on resected surface 1022, provides a visual indication of whether the talar component is the appropriate size. In particular, when outer edge 629 (having the same dimension as an available talar component) corresponds to an outer edge of resected surface 1022, as shown in FIG. 31, this indicates that template 600 is the correct size. If the best template size would be between available sizes, a template slightly smaller than what would otherwise be required is used to minimize the risk of implant gutter impingement.

With template 600 identified as having the correct size for the applicable talus 1020, template frame 610 is held in position on resected surface 1022 while alignment of template 600 with second metatarsal 1012 is confirmed or necessary adjustments are made to confirm alignment. Additionally, template frame 610 is centered on resected surface 1022 of talus 1020 at this time. These measures are ultimately used to obtain optimal alignment for datum pin 800 insertion into the talus, thereby optimizing rotational alignment of the various resection cutting guides attached with reference to the datum and utilized subsequent to the insertion of the datum, and, accordingly, contributing to ensure that the final implant is properly positioned when implanted.

Figure 33:
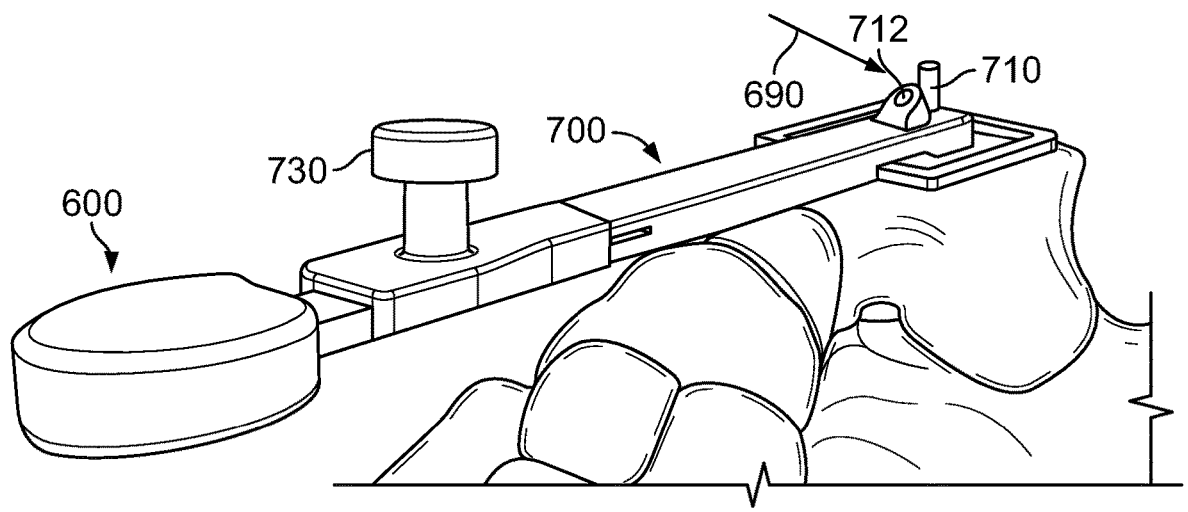

A drill guide 700 is then attached to template 600, as shown in FIG. 32, by insertion of a threaded end of thumb screw 730 into threaded aperture 642, creating a threaded connection. When attached, drill guide 700 is oriented so that its shaft 720 is directly over shaft 640 of template 600, and extends into window 612 of template frame 610, as shown in FIGS. 32 and 33. Once drill guide 700 is in position over the talus, a joint space evaluator, such as joint space evaluator 500, is used to fully seat the template on the talus. In one example, a first end 502 of joint space evaluator 500 is directed to opening mount 710 of drill guide 700, and a notch 505 at first end 502 is applied to opening mount 710 to seat template 600. This step is indicated by arrow 690 in FIG. 33. A lamina spreader (not shown) is then used to hold the template to the top of the talus. To accomplish this, the lamina spreader is used to engage pins 632A, 634A with the resected surface of the talus and further to keep template 600 flush with the resected talus. In a variant, other approaches or tools may be used to ensure proper seating of template 600.

Figure 34:
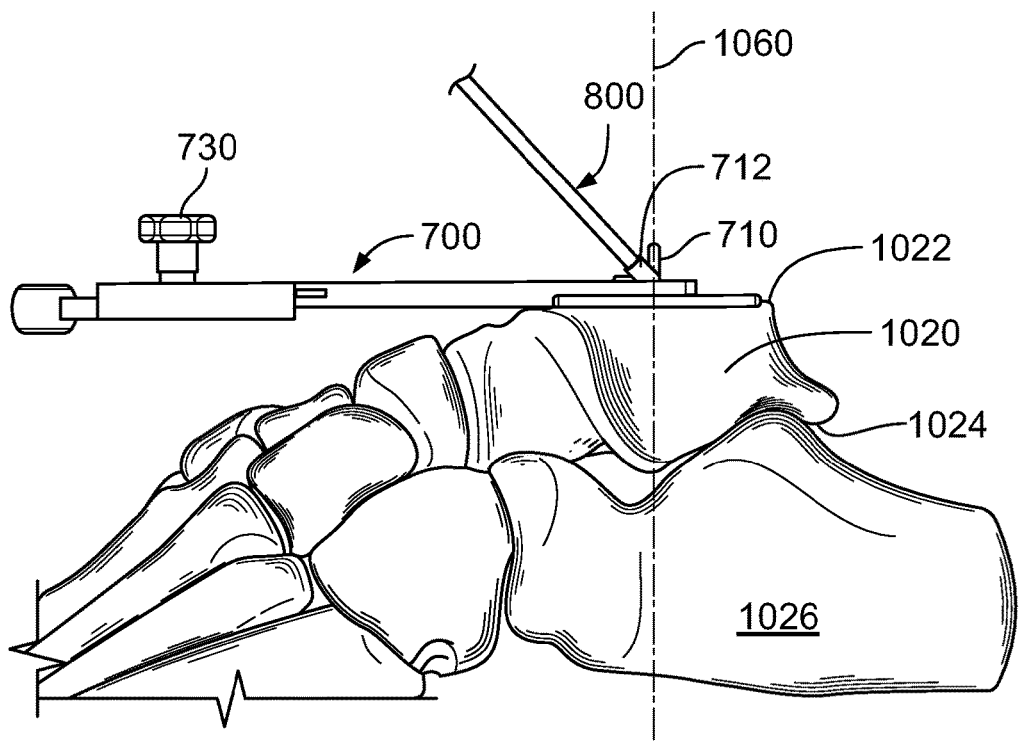
FIG. 34 is a side view of a datum pin inserted into the drill guide according to a further step of the method.

The ankle is now viewed from the side to ensure that opening mount 710 of drill guide 700 is centered over the lateral process as indicated by axis 1060 on FIG. 34 while the drill guide is positioned in an anterior to posterior direction. In particular, the structure of opening mount 710 may be used to verify the alignment of the drill guide with respect to the lateral process. Additionally, these positioning steps may be done under fluoroscopy. A final check to ensure there is no gap between template 600 and a posterior edge of resected surface 1022 is made at this time (FIG. 34). With template 600 in position, a datum pin 800 is inserted through opening 712 in opening mount 710. In one example, the datum pin is 2.4 mm in diameter. The datum pin is inserted in a manner to ensure that subtalar joint 1024 is not crossed during the process and the datum pin remains in talus 1022 without entering the calcaneus bone 1026. Thus, one advantage of template 600 is that datum pin 800 is insertable into the talus while template 600 is in position on the talus, as template window 612 removes any impediment to bone entry. Throughout the procedure, window 612 also provides an advantage in that it offers greater visibility of the talus, affording opportunities to correct any deficiency in the positioning of the various instruments or in the preparation of the talar surface itself.

Figure 35:
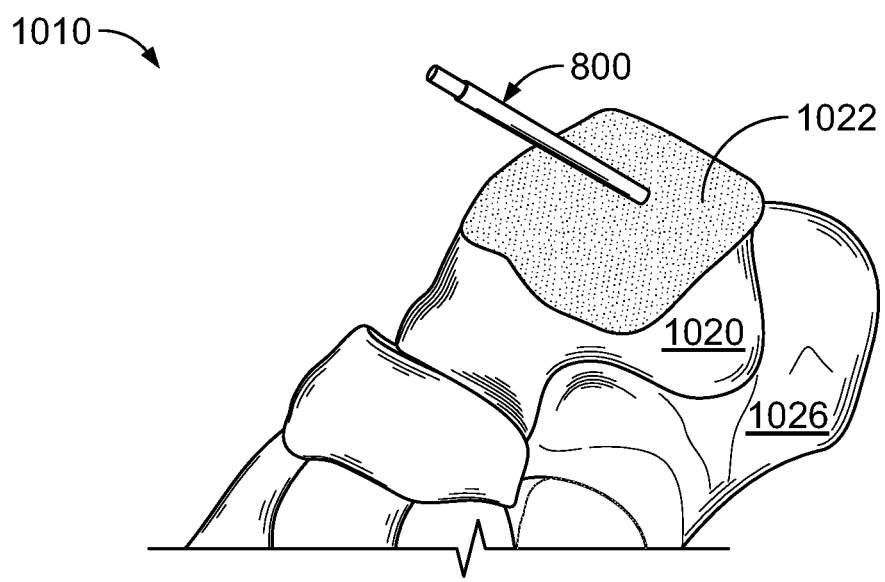
FIG. 35 is a perspective view of the post talar cut template removed from the bone surface according to a further step of the method.

Once datum pin 800 is in place, drill guide 700 is removed by unscrewing thumb screw 730. Then, separately or together with drill guide 700, template 600 is removed, leaving datum pin 800 in place as shown in FIG. 35. Optionally, if the datum pin requires further adjustment, the datum pin may be removed and an adjustment pin guide (not shown) may be placed to realign the trajectory of the datum pin.

In some embodiments, when the unevenness in the joint space is significant, an additional step of using a thicker joint space evaluator after initial tissue balancing may aid in the verification of the evenness of the joint space. For instance, an initial approach may use a joint space evaluator with a 12 mm thickness. If the unevenness in a joint is much greater than five degrees when using this evaluator, a larger evaluator may be inserted following initial tissue balancing to determine whether additional tissue balancing should be performed, and/or whether additional resection may be performed.

In another embodiment, a method of use may involve use of joint space evaluator 500 as described above, followed by use of post talar cut template 600, also described above in a single procedure.

In other embodiments, a method may involve any number of steps preceding use of the joint space evaluator, the post talar cut template, or both. For example, additional steps of a surgical procedure may involve any combination of the setup of instrumentation for ankle surgery, alignment of instrumentation based on a patient's anatomy, performance of tibial resections, and performance of talar resections. In some examples, any number of these procedural steps may be performed using instrumentation and with methods as described above and in U.S. Pat. App. Pub. No. 2012/0130376.

In still further embodiments, a method may involve any number of steps following use of the joint space evaluator, the post talar cut template, or both. For example, additional steps of a surgical procedure may involve any combination of datum positioning, anterior-posterior cut guide positioning, talar circumferential cutting, use of a window drill guide, implant sizing and trialing, including use of a window trial, and implant placement. In some examples, any number of these procedural steps may be performed using instrumentation and with methods as described above and in U.S. Pat. App. Pub. No. 2012/0130376.

In other embodiments, a method may involve a procedure incorporating any number of additional steps both before and after use of one or both of joint space evaluator and post talar cut template.

Combinations of Trial Implant, Guide Structures and Joint Space Evaluator

In one aspect, the present disclosure relates to kits that include combinations of one or both of the joint spacer and talar cut guide together with any combination of a trial implant and a surgical guide. In one embodiment, for example, a kit includes a joint spacer, a talar cut guide, a trial implant and a surgical guide structure. In another example, a kit includes ten joint spacers and ten trial implants.

In another aspect, the present disclosure relates to methods that involve the use of any combination of the joint space evaluator, talar cut guide, trial implant and surgical guide structure. In each of the contemplated embodiments, the steps of using the referenced instruments may be performed in any manner described herein. In some embodiments, a method includes use of the joint spacer evaluator and one or both of a trial implant and a surgical guide structure. In other embodiments, a method includes use of a talar cut guide and one or both of a trial implant and a surgical guide structure. In still further embodiments, a method involves use of the joint space evaluator, the talar cut guide and one or both of a trial implant and a surgical guide structure.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:

1. A trial implant, comprising:
a central portion, comprising:
   a top articulating surface extending between a first end and a second end and having a convex shape,
   a bottom surface configured to at least partially contact a first resected surface of a bone, and
   a first side surface extending between the top articulating surface and the bottom surface, the first side surface being sloped such that a width of the top articulating surface is greater than a width of the bottom surface; and
a first outer portion extending laterally from the central portion,
wherein the first side surface and the first outer portion are separated by a first opening shaped such that up to four resected surfaces of the bone are visible when the trial implant is seated on the bone.

2. The trial implant of claim 1, wherein the trial implant includes a second opening.

3. The trial implant of claim 2, wherein the second opening is smaller than the first opening.

4. The trial implant of claim 1, wherein the first outer portion extends laterally from the central portion such that the first outer portion is entirely on one side of a plane through the first side surface.

5. The trial implant of claim 1, wherein the first outer portion forms a perimeter around the central portion.

6. The trial implant of claim 1, wherein at least the central portion and the first outer portion are monolithic.

7. The trial implant of claim 1, wherein a width of the top articulating surface of the central portion and a width of the bottom surface of the central portion are each greater than a height of the first side surface of the central portion.

8. The trial implant of claim 1, wherein the first outer portion comprises:
   a top surface that faces a same direction as the top articulating surface of the central portion;
   a bottom surface that faces a same direction as the bottom surface of the central portion; and
   a side surface.

9. The trial implant of claim 8, wherein a width of the top surface of the first outer portion and a width of the bottom surface of the first outer portion are each greater than a height of the side surface of the first outer portion.

10. The trial implant of claim 1, wherein at least a portion of the bottom surface of the first outer portion extends below the bottom surface of the central portion.

11. The trial implant of claim 1, wherein the top articulating surface of the central portion comprises a first top surface, a second top surface laterally spaced from the first top surface, and a ridge separating the first top surface from the second top surface.

12. The trial implant of claim 1, wherein the bottom surface of the central portion comprises a post configured for placement in a hole through the first resected surface of the bone.

13. The trial implant of claim 1, wherein the bone is a talar bone of an ankle of a patient.

14. The trial implant of claim 1, further comprising a second outer portion extending laterally from the central portion such that the central portion separates the second outer portion from the first outer portion and a second opening separates the central portion from the second outer portion.

15. The trial implant of claim 14, further comprising a third opening through the central portion, the third opening having a long dimension transverse to a long dimension of the second opening.

16. The trial implant of claim 14, wherein the first outer portion has a first shape and the second outer portion has a second shape different from the first shape.

17. The trial implant of claim 14, wherein the second outer portion has a substantially uniform thickness.

18. The trial implant of claim 14, wherein a bottom surface of the second outer portion does not extend below the bottom surface of the central portion.

19. The trial implant of claim 14, wherein the second outer portion extends laterally from the central portion such that the second outer portion is entirely on one side of a plane through a second side surface of the central portion.

20. The trial implant of claim 19, wherein the second side surface of the central portion has a different slope from the first side surface of the central portion.

* * * * *